United States Patent
Baek et al.

(10) Patent No.: US 11,883,402 B2
(45) Date of Patent: Jan. 30, 2024

(54) CRYSTALLINE FORMS OF A QUINAZOLINE COMPOUND AND ITS HYDROCHLORIDE SALTS

(71) Applicant: Hanmi Pharmaceutical Co., Ltd., Gyeonggi-do (KR)

(72) Inventors: Jong Ouk Baek, Gyeonggi-do (KR); Hee Cheol Kim, Gyeonggi-do (KR); Tae Hee Ha, Gyeonggi-do (KR); Kweehyun Suh, Gyeonggi-do (KR); Guru Reddy, Irvine, CA (US)

(73) Assignees: Hanmi Pharmaceutical Co., Ltd. (KR); Spectrum Pharmaceuticals, Inc., Irvine, CA (US)

( * ) Notice: Subject to any disclaimer, the term of this patent is extended or adjusted under 35 U.S.C. 154(b) by 61 days.

(21) Appl. No.: 17/275,382

(22) PCT Filed: Sep. 12, 2019

(86) PCT No.: PCT/IB2019/057720
§ 371 (c)(1),
(2) Date: Mar. 11, 2021

(87) PCT Pub. No.: WO2020/053816
PCT Pub. Date: Mar. 19, 2020

(65) Prior Publication Data
US 2022/0056011 A1    Feb. 24, 2022

Related U.S. Application Data

(60) Provisional application No. 62/731,500, filed on Sep. 14, 2018.

(51) Int. Cl.
| | |
|---|---|
| *A61K 31/517* | (2006.01) |
| *A61K 33/243* | (2019.01) |
| *A61K 31/282* | (2006.01) |
| *A61K 31/337* | (2006.01) |
| *A61K 31/404* | (2006.01) |
| *A61K 31/44* | (2006.01) |
| *A61K 31/4439* | (2006.01) |
| *A61K 31/475* | (2006.01) |
| *A61K 31/506* | (2006.01) |
| *A61K 31/513* | (2006.01) |
| *A61K 31/519* | (2006.01) |
| *A61K 31/52* | (2006.01) |
| *A61K 31/655* | (2006.01) |
| *A61K 31/7068* | (2006.01) |
| *A61K 31/7072* | (2006.01) |
| *A61K 31/7076* | (2006.01) |
| *A61K 31/7105* | (2006.01) |
| *A61K 38/17* | (2006.01) |
| *A61K 39/395* | (2006.01) |
| *C07D 401/12* | (2006.01) |

(52) U.S. Cl.
CPC .......... *A61K 31/517* (2013.01); *A61K 31/282* (2013.01); *A61K 31/337* (2013.01); *A61K 31/404* (2013.01); *A61K 31/44* (2013.01); *A61K 31/4439* (2013.01); *A61K 31/475* (2013.01); *A61K 31/506* (2013.01); *A61K 31/513* (2013.01); *A61K 31/519* (2013.01); *A61K 31/52* (2013.01); *A61K 31/655* (2013.01); *A61K 31/7068* (2013.01); *A61K 31/7072* (2013.01); *A61K 31/7076* (2013.01); *A61K 31/7105* (2013.01); *A61K 33/243* (2019.01); *A61K 38/179* (2013.01); *A61K 39/3955* (2013.01); *C07D 401/12* (2013.01); *C07B 2200/13* (2013.01)

(58) Field of Classification Search
CPC ..... A61K 31/517; A61K 31/519; A61P 35/00; C07D 401/12; C07D 239/94
See application file for complete search history.

(56) References Cited

U.S. PATENT DOCUMENTS

| | | | | |
|---|---|---|---|---|
| 7,452,555 B2 * | 11/2008 | Childs | .................. | C07C 217/20 562/405 |
| 8,003,658 B2 * | 8/2011 | Ham | .................... | C07D 403/12 514/266.4 |
| 8,859,767 B2 * | 10/2014 | Bang | .................... | A61K 31/517 544/293 |
| 9,731,022 B2 * | 8/2017 | Kim | ..................... | C07D 401/12 |
| 9,931,406 B2 * | 4/2018 | Kim | ....................... | A61K 47/44 |
| 2008/0058355 A1 | 3/2008 | Westheim | | |
| 2011/0152297 A1 | 6/2011 | Halsall et al. | | |
| 2013/0131341 A1 | 5/2013 | Jyothi Prasad et al. | | |

(Continued)

FOREIGN PATENT DOCUMENTS

| | | |
|---|---|---|
| KR | 10-1013319 B1 | 2/2011 |
| KR | 10-2011-0135685 A | 12/2011 |

(Continued)

OTHER PUBLICATIONS

Extended European Search Report dated May 11, 2022 in European application No. 19860538.8, 7 pages.

(Continued)

*Primary Examiner* — My-Chau T. Tran
(74) *Attorney, Agent, or Firm* — Fox Rothschild LLP

(57) ABSTRACT

This patent document relates to the crystalline forms of a quinazoline compound and the hydrochloride salts thereof. More particularly, this patent document relates to a preparation method of the crystalline forms of 1-(4-(4-(3,4-dichloro-2-fluorophenylamino)-7-methoxyquinazolin-6-yloxy)piperidin-1-yl)prop-2-en-1-one and its hydrochloride salts.

21 Claims, 14 Drawing Sheets

(56) References Cited

U.S. PATENT DOCUMENTS

2014/0275534 A1   9/2014  Bang et al.
2018/0016259 A1   1/2018  Li et al.
2022/0056011 A1   2/2022  Baek et al.

FOREIGN PATENT DOCUMENTS

| WO | 2008/150118 A2 | 12/2008 |
| WO | 2013/051883 A2 | 4/2013 |
| WO | 2015-154725 A1 | 10/2015 |
| WO | 2017/067447 A1 | 4/2017 |
| WO | 2018-075823 A1 | 4/2018 |
| WO | 2018-094225 A1 | 5/2018 |

OTHER PUBLICATIONS

Extended European Search Report dated May 11, 2022, in European patent application No. 19859287.5, 7 pages.

\* cited by examiner

CRYSTALLINE FORMS OF A QUINAZOLINE COMPOUND AND ITS HYDROCHLORIDE SALTS

CROSS-REFERENCE TO RELATED APPLICATIONS

This application claims the benefit of U.S. Provisional Application No. 62/731,500, filed on Sep. 14, 2018, the entire disclosures of which is incorporated herein by reference.

TECHNICAL FIELD

This patent document relates to crystalline forms of a quinazoline compound and its hydrochloride salt forms. More particularly, the crystalline forms are from 1-(4-(4-(3,4-dichloro-2-fluorophenylamino)-7-methoxyquinazolin-6-yloxy)piperidin-1-yl)prop-2-en-1-one, and a pharmaceutical composition containing the same.

BACKGROUND ART

The compound of the following chemical formula (1), having general formula of 1-(4-(4-(3,4-dichloro-2-fluorophenylamino)-7-methoxyquinazolin-6-yloxy)piperidin-1-yl)prop-2-en-1-one is disclosed in Korean Patent No. 1,013,319 and U.S. Pat. No. 8,003,658, and these patents disclose that the above compound has antiproliferative activity such as anticancer activity, and can selectively and effectively treat the drug resistance induced by tyrosine kinase mutation:

[Chemical Formula (1)]

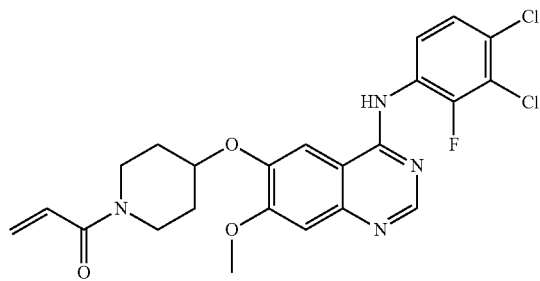

However, the compound of chemical formula (1) prepared in the above cited patents is generally prepared in the form of amorphous solid or incomplete crystal which is less well suited for large-scale pharmaceutical processing, and there is no description with regard to the preparation of specific crystalline forms.

The compound of chemical formula (1) prepared by the above cited patents has a disadvantage in that the solubility in water is very low. In addition, since the compound of formula (I) prepared by the cited patents unavailable in the form of uniform crystals, meeting physicochemical stability standards required for pharmaceuticals can be troublesome.

Thus, there is a need to prepare the salts of the compound of chemical formula (1) in a crystalline form having improved solubility in water while still being capable of meeting sufficiently the strict requirements and specifications for pharmaceutical formulations.

The above information disclosed in this Background section is only for the enhancement of understanding of the background of the invention and therefore it by no means is intended as an admission that information contained herein constitutes prior art already known to a person of ordinary skill in the art.

SUMMARY OF THE DISCLOSURE

It is an object of this patent document to provide crystalline forms of the above quinazoline compound of chemical formula (1) and its crystalline hydrochloride salt forms as well as a pharmaceutical composition containing the same.

Formula (1)

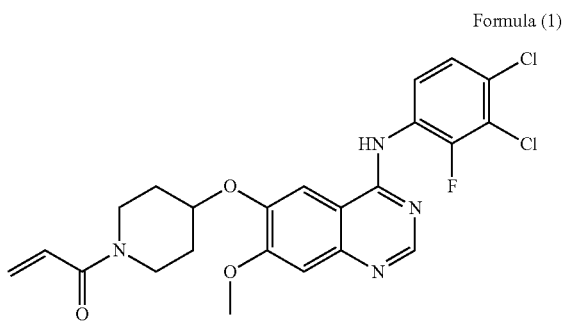 [SMILES: C=CC(=O)N1CCC(Oc2cc3c(Nc4ccc(Cl)c(Cl)c4F)ncnc3cc2OC)CC1]

Specifically, the preferred crystalline form of the quinazoline compound of chemical formula (1) is
1) the crystalline hydrate form of the quinazoline compound of chemical formula (1), and
2) the crystalline anhydrous form of the quinazoline compound of chemical formula (1).

In addition, the crystalline hydrochloride salt form of the preferred quinazoline compound of chemical formula (1) is
1) the crystalline hydrochloride salt hydrate form of the quinazoline compound of chemical formula (1),
2) the crystalline anhydrous hydrochloride salt form of the quinazoline compound of chemical formula (1).

More preferred examples of the crystalline form are as follows:

the crystalline dihydrate ($2H_2O$) form of the compound of chemical formula (1) having the X-ray powder diffraction (XRPD) pattern including peaks at the diffraction angle ($2\theta\pm0.2°$ of 9.4, 13.0, and 18.5° when irradiated with a Cu-Kα light source;

the crystalline anhydrous Form I of the compound of chemical formula (1) having the XRPD pattern including peaks at the diffraction angle ($2\theta\pm0.2°$) of 6.0, 18.3, and 22.7° when irradiated with a Cu-Kα light source;

the crystalline anhydrous Form II of the compound of chemical formula (1) having the X-ray powder diffraction pattern including peaks at the diffraction angle ($2\theta\pm0.2°$) of 4.9, 5.9 and 11.8° when irradiated with a Cu-Kα light source;

the crystalline monohydrochloride salt monohydrate ($1HCl \cdot 1H_2O$) form of the compound of chemical formula (1) having the X-ray powder diffraction pattern including peaks at the diffraction angle ($2\theta\pm0.2°$) of 8.9, 13.4, 21.1 and 23.5° when irradiated with a Cu-Kα light source; and the crystalline anhydrous monohydrochloride salt (1 HCl) form of the compound of chemical formula (1) having the XRPD pattern including peaks at the diffraction angle ($2\theta\pm0.2°$) of 9.5, 23.0, 23.2 and 23.5° when irradiated with a Cu-Kα light source; and also, the crystalline dihydrate ($2H_2O$) form of the compound of chemical formula (1) having $^{13}C$ CP/MAS TOSS (cross polarization/magic angle spinning total suppression of sidebands) solid state nuclear magnetic resonance (ssNMR) spectrum including the chemical shifts (ppm±0.5 ppm) of 165.4, 156.2 and 1477 ppm in the $^{13}$C CP/MAS TOSS ssNMR spectrum;

the crystalline anhydrous Form 1 of the compound of chemical formula (1) having $^{13}$C CP/MAS TOSS solid state nuclear magnetic resonance spectrum including the chemical shifts (ppm±0.5 ppm) of 156.7, 146.9, 127.3 and 54.3 ppm in the $^{13}$C CP/MAS TOSS solid state nuclear magnetic resonance spectrum;

the crystalline anhydrous Form II of the compound of chemical formula (1) having $^{13}$C CP/MAS TOSS ssNMR spectrum including the chemical shifts (ppm±0.5 ppm) of 165.2, 156.7, 153.1 and 129.2 ppm in the $^{13}$C CP/MAS TOSS solid state nuclear magnetic resonance spectrum;

the crystalline monohydrochloride salt monohydrate (1 HCl·1H$_2$O) form of the compound of chemical formula (1) having $^{13}$C CP/MAS TOSS solid state nuclear magnetic resonance spectrum including the chemical shifts (ppm±0.5 ppm) of 164.5, 157.8 and 145.8 ppm in the $^{13}$C CP/MAS TOSS solid state nuclear magnetic resonance spectrum; and the crystalline anhydrous monohydrochloride salt (1 HCl) form of the compound of chemical formula (1) having $^{13}$C CP/MAS TOSS solid state nuclear magnetic resonance spectrum including the chemical shifts (ppm±0.5 ppm) of 163.0, 158.7 and 146.9 ppm in the $^{13}$C CP/MAS TOSS solid state nuclear magnetic resonance spectrum.

The crystalline form of the compound of chemical formula (1) or its hydrochloride salt is "substantially pure" wherein the expression "substantially pure" means at least 95%, preferably 99%.

That is to say, the purity of 95% to 99% means that the particular crystalline form of the compound of chemical formula (1) or its hydrochloride salt is 95% to 99% or more and other crystalline forms (amorphous or crystalline forms of the compound of Formula (1) other than the particular crystalline form) are 5% to 1% or less.

In addition, this patent document provides the amorphous monohydrochloride salt form of the said quinazoline compound of chemical formula (1).

According to another object of the present invention, this patent document provides a pharmaceutical composition comprising the crystalline form of the compound of formula (1) or the crystalline form of the hydrochloride salt thereof; and at least one pharmaceutically acceptable carrier or diluent.

The pharmaceutical composition has an antiproliferative activity such as anticancer activity and may be used for selective and effective treatment of drug resistance induced by tyrosine kinase mutagenesis.

The crystalline form of the compound of chemical formula (1) according to this patent document and its crystalline hydrochloride salt form is superior in terms of various physical and chemical properties such as solubility in water, hygroscopicity and chemical stability, and thus can be easily used in the production of a pharmaceutical composition containing it as an active ingredient.

Also provided is a method of treating a neoplasm in a subject comprising administering to a subject in need thereof the novel crystalline form of the compound of Formula (1), a pharmaceutical composition thereof, or its combination with one or more other agents.

A further aspect of the patent document provides methods of preparing the crystalline forms described herein.

BRIEF DESCRIPTION OF THE DRAWINGS

The above and other features of the crystalline forms will now be described in detail with reference to certain exemplary embodiments thereof illustrated the accompanying drawings which are given hereinbelow by way of illustration only, and thus are not limitative of the present invention, and wherein:

FIG. 1A shows the XRPD for the crystalline form prepared in Example 1; FIG. 1B shows XRPD for the crystalline form prepared in Example 2; FIG. 1C shows XRPD for the crystalline form prepared in Example 3; FIG. 1D shows XRPD for the crystalline form prepared in Example 4; and FIG. 1E shows XRPD for the crystalline form prepared in Example 5.

FIG. 1F shows XRPD for the amorphous form prepared in Example 6; and FIG. 1G shows XRPD for the compound of chemical formula (1) prepared in Reference Example.

FIG. 2A shows the ssNMR for the crystalline form prepared in Example 1; FIG. 2B shows ssNMR for the crystalline form prepared in Example 2; FIG. 2C shows ssNMR for the crystalline form prepared in Example 3; FIG. 2D shows ssNMR for the crystalline form prepared in Example 4; and FIG. 2E shows ssNMR for the crystalline form prepared in Example 5.

FIG. 2F shows DVS for the amorphous form prepared in Example 6; and FIG. 2G shows ssNMR for the compound of chemical formula (1) prepared in Reference Example.

FIGS. 3A, 3B, 30, 3D and 3E show the Differential Scanning calorimetry (DSC) graphs of the compound of chemical formula (1) and its crystalline hydrochloride salt form according to the example; FIG. 3A shows the DSC for the crystalline form prepared in Example 1; FIG. 3B shows DSC for the crystalline form prepared in Example 2; FIG. 3D shows DSC for the crystalline form prepared in Example 4; and FIG. 3E shows DSC for the crystalline form prepared in Example 5.

FIGS. 4A, 4B, 40, 4D and 4E show the dynamic vapor sorption (DVS) graphs of the compound of chemical formula (1) and its crystalline hydrochloride salt form according to the example; FIG. 4A shows the DVS for the crystalline form prepared in Example 1; FIG. 4B shows DVS for the crystalline form prepared in Example 2; FIG. 4D shows DVS for the crystalline form prepared in Example 4; FIG. 4E shows DVS for the crystalline form prepared in Example 5.

FIG. 4F shows ssNMR for the amorphous form prepared in Example 6; and FIG. 4G shows DVS for the compound of chemical formula (1) prepared in Reference Example.

DETAILED DESCRIPTION

Figure 1A:
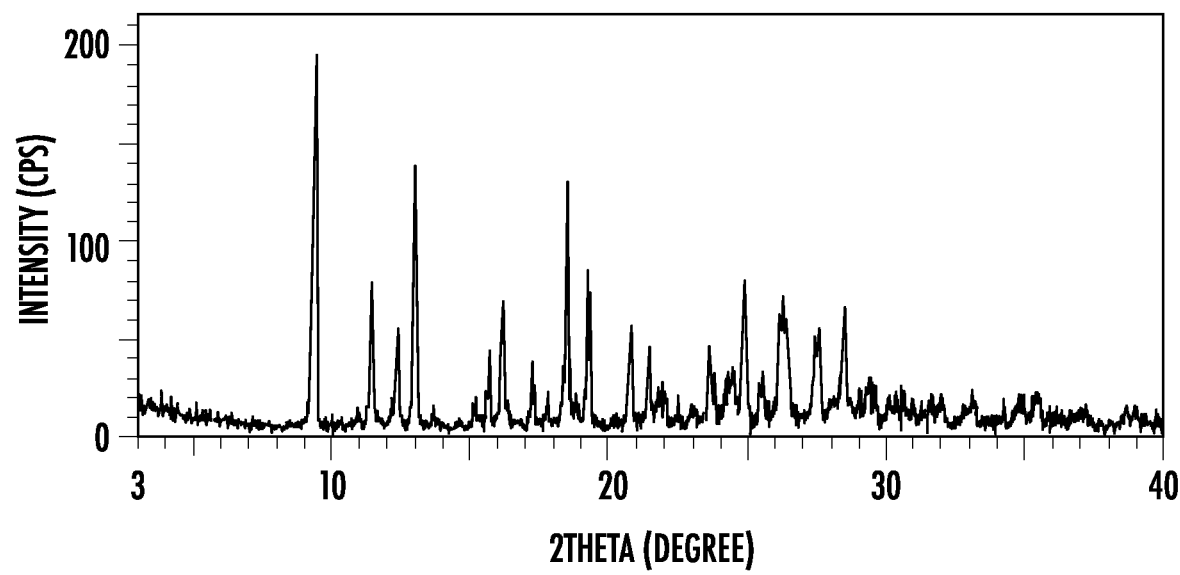
FIGS. 1A, 1B, 1C, 1D and 1E show the X-ray powder diffraction (XRPD) spectrums of the compound of chemical formula (1) and its crystalline hydrochloride salt form according to the example.
Figure 1B:
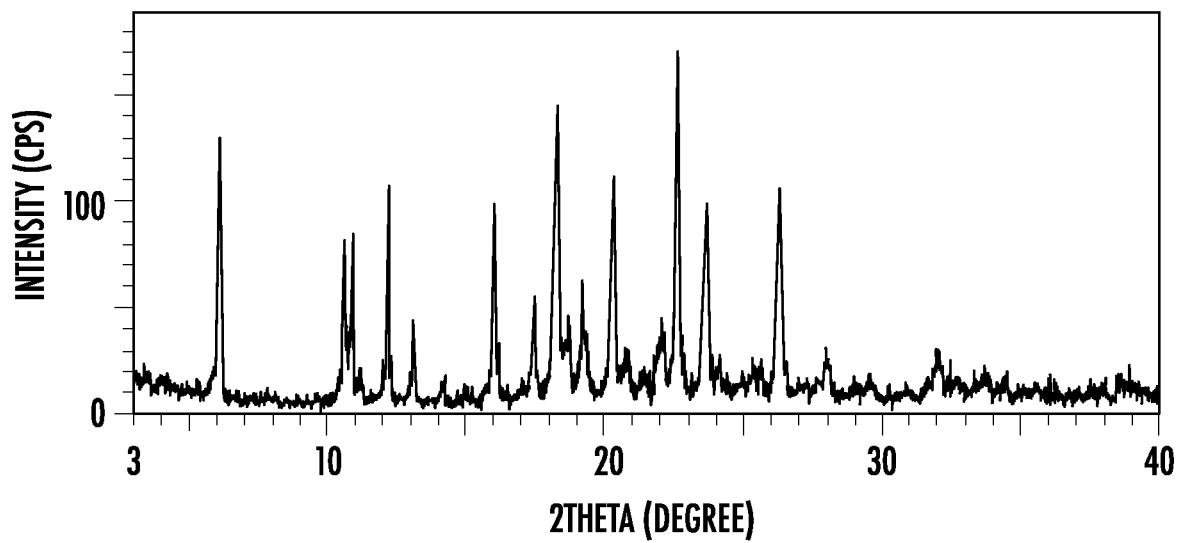
Figure 1C:
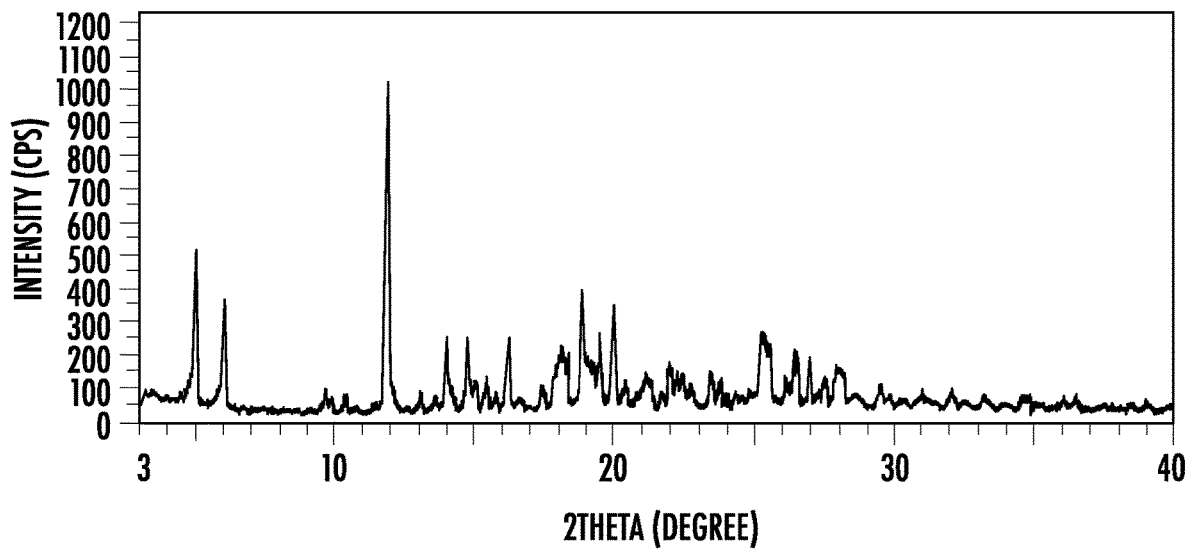
Figure 1D:
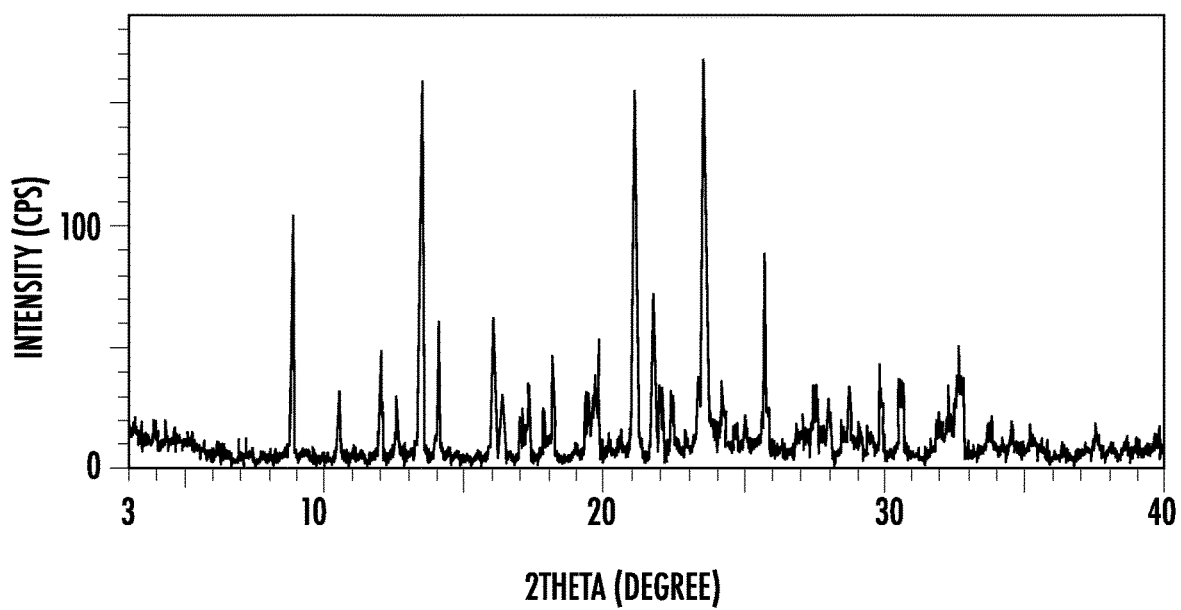
Figure 1E:
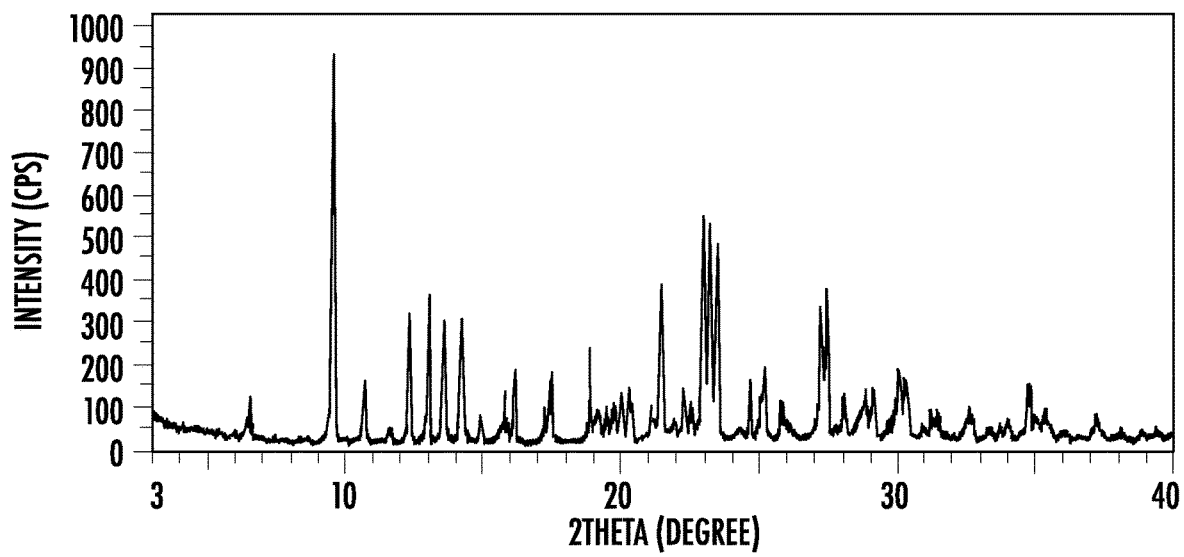

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

Definition

Terms not specifically defined in this specification have meanings recognized by those skilled in the art in light of the technology and context. However, unless otherwise specified, throughout the present specification the following terms have the meanings indicated below:

The term "about" as used herein means within 5%, preferably between 1% and 2% of a given value or range. For example, the expression "about 10%" refers to 9.5% to 10.5%, preferably 9.8% to 102%. As another example, the expression "about 100° C." refers to 95% to 105%, preferably 98° C. to 102° C.

As used herein the term "chemical purity" refers to the weight % that is the specified chemical entity, including specified polymorph form. For example, when a crystalline dihydrate ($2H_2O$) of the compound of Formula (1) is characterized as having greater than 95% chemical purity, that means that greater than 95% by weight of the substance is the crystalline dihydrate ($2H_2O$) of the compound of Formula (1) and less than 5% by weight of any other compound including other anhydrous forms and/or polymorphs. Similarly, when a particular monohydrochloride monohydrate crystalline form ($1HCl \cdot 1H_2O$) of the compound of Formula (1) is characterized as having greater than 95% chemical purity, this particular crystalline form is more than 95% by weight among all forms (including for example crystalline or non-crystalline form, salt form or salt-free form, hydrate or anhydrous form) of the compound of Formula (1) in the same composition. The term "derived" in this context refers to forming a desirable crystalline form (e.g. an anhydrous form, a hydrate form, or a pharmaceutically acceptable salt) of the compound of Formula (1) without changing the chemical structure of the compound. The term "poziotinib" as used herein refers to any of the crystalline forms of the compound of formula (1).

The peak value of the diffraction angle (2θ) at the X-ray powder diffraction (XRPD) spectrum reported in this patent document has preferably the experimental error of ±0.5%, more preferably ±0.2% which is typically observable in the art.

Also, the chemical shift in the solid state nuclear magnetic resonance spectrum reported in this patent document will be preferably interpreted as within ±0.5 ppm, more preferably as within ±0.2%.

The Crystalline Form of the Quinazoline Compound of Chemical Formula (1) and its Crystalline Hydrochloride Salt Form This patent document provides the following compound of formula (1), 1-(4-(4-(3,4-dichloro-2-fluorophenylamino)-7-methoxyquinazoline-6-yloxy)piperidin-1-yl)prop-2-en-1-one and its crystalline hydrochloride salt form:

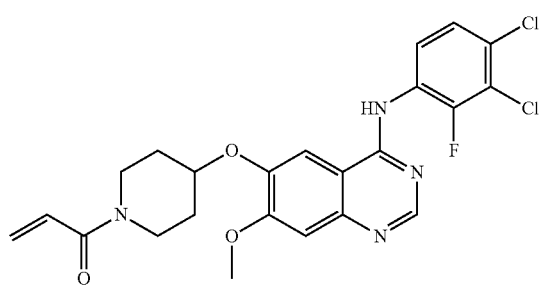

[Chemical formula (1)]

The compound of chemical formula (1) above may be prepared according to the general procedure described in Korean Patent No. 1,013,319 and U.S. Pat. No. 8,003,658, all of which are incorporated herein by reference in their entirety.

The compound of chemical formula (1) described in the above documents is a poorly soluble compound which is amorphous and has a solubility in water of less than 1.0 µg/mL.

In general, it is known that the conversion of the free base to the form of salts aids in the solubilization of the water-insoluble drug substance. However, these salts must have various physicochemical properties such as reproducibility of the preparation of specific crystalline form, high crystallinity, stability of crystalline form, chemical stability, and non-hygroscopicity, etc. which are pharmacologically required.

In order to select the suitable salt form of the compound of chemical formula (1), various salts of the compound of chemical formula (1) were prepared using various acids and solvents according to various conditions and procedures, and their physicochemical properties were evaluated. Among the salts thus prepared, the crystalline forms of the various forms of the hydrochloride salt of the compound of chemical formula (1) are the most excellent in terms of various physicochemical properties such as reproducibility of the preparation of specific crystalline form, high crystallinity, stability of crystalline form, chemical stability, and non-hygroscopicity, etc. which are pharmacologically required.

The Crystalline Form of the Quinazoline Compound of Chemical Formula (1) and its Crystalline Hydrochloride Salt Form The salt of the compound of chemical formula (1) may be prepared in crystalline form, amorphous form or a mixture thereof, but it is preferable that the salt is in crystalline form. The crystalline hydrochloride salt form of the compound of chemical formula (1) is preferable in that it has excellent stability and physicochemical properties that are easy to formulate.

According to the present invention, the compound of chemical formula (1) may be in the form of various crystalline forms, for example, its crystalline dihydrate ($2H_2O$) form and crystalline anhydrous form.

Also, according to the present invention, the compound of chemical formula (1) may be in the form of various crystalline hydrochloride salts, for example, crystalline monohydrochloride monohydrate ($1HCl \cdot 1H_2O$) form and their crystalline anhydrous monohydrochloride salt (1 HCl) form.

Among the crystalline hydrochloride salts, as a result of examining in Test Example 1 as described later, the crystalline anhydrous monohydrochloride salt form was the most excellent in solubility in water, and as a result of examining in Test Example 2, it may be advantageous in terms of non-hygroscopicity and stability, and thus may be desirable as a useful active ingredient in pharmaceutical compositions.

Hereinafter, each of the crystalline forms according to this patent document will be described in more detail.

As an example, this patent document provides the crystalline dihydrate ($2H_2O$) form of the compound of chemical formula (1).

The crystalline dihydrate ($2H_2O$) form of the compound of chemical formula (1) has the XRPD spectrum including peaks at the diffraction angle (2θ±0.2°) of 9.4, 11.4, 13.0, 16.1, 18.5, 19.3, 24.9 and 26.3° when irradiated with a Cu-Kα light source. These peaks may be peaks with relative intensities of about 10% to 20% or more.

The above crystalline form may have chemical shifts (ppm±0.5 ppm) of 147.7, 156.2, and 165.4 ppm in the $^{13}$C CP/MAS TOSS solid state nuclear magnetic resonance (cross polarization/magic angle spinning total suppression of sidebands solid state nuclear magnetic resonance, ssNMR) spectrum.

The above crystalline form may have a moisture content (theoretical moisture content of 6.83%) of about 7.5%, a condensation temperature of about 117-122° C. and a melting point of about 190-195° C.

The above crystalline form may have an endothermic peak of the lowest point at about 111° C. when running from a starting point of about 79° C., as measured by the DSC (10° C./min).

The above crystalline form can be measured to have hygroscopic degree of about 2% to 5% in the relative humidity range of 0-90%, as measured by the DVS.

As another example, this patent document provides the crystalline anhydrous Form I of the compound of chemical formula (1).

The crystalline anhydrous Form I of the compound of chemical formula (1) has the XRPD spectrum including peaks at the diffraction angle (2θ±0.2°) of 6.0, 10.6, 10.9, 12.1, 16.0, 17.5, 18.3, 19.2, 20.3, 22.7, 23.7 and 26.3° when irradiated with a Cu-Kα light source. These peaks may be peaks with relative intensities of about 10% to 20% or more.

The above crystalline form may have chemical shifts (ppm±0.5 ppm) of 54.3, 127.3, 148.9 and 158.7 ppm in the $^{13}$C CP/MAS TOSS solid state nuclear magnetic resonance (ssNMR) spectrum.

The above crystalline form may have a moisture content of about 0.1% and a melting point of about 190-195° C.

The above crystalline form may have an endothermic peak of the lowest point at about 191° C. when running from a starting point of about 186° C., as measured by the DSC (10° C./min).

The above crystalline form can be measured to have a hygroscopic degree of about 0.5% in a relative humidity range of 10-50% as measured by the DVS and a hygroscopic degree of about 3% in a relative humidity range of 50-90%.

As another example, this patent document provides the crystalline anhydrous Form II of the compound of chemical formula (1).

The crystalline anhydrous Form II of the compound of chemical formula (1) may have the XRPD spectrum including peaks at the diffraction angle (2θ±0.2°) of 4.9, 5.9, 11.8, 18.8 and 19.9° when irradiated with a Cu-Kα light source. These peaks may be peaks with relative intensities of about 10% to 20% or more.

The above crystalline form may have chemical shifts (ppm±0.5 ppm) of 129.2, 153.1, 156.7 and 165.2 ppm in the $^{13}$C CP/MAS TOSS solid state nuclear magnetic resonance (ssNMR) spectrum.

The above crystalline form may have a moisture content of about 0.3% and a melting point of about 183-185° C.

The above crystalline form may have an endothermic peak of the lowest point at about 185° C. when running from a starting point of about 181° C., as measured by the DSC (10° C./min).

The above crystalline form can be measured to have very low hygroscopic degree in a relative humidity range of 0-90%, as measured by the DVS.

As another example, this patent document provides the crystalline monohydrochloride monohydrate (1HCl·1H$_2$O) form of the compound of chemical formula (1).

The crystalline monohydrochloride monohydrate (1 HCl·1H$_2$O) form of the compound of chemical formula (1) may have the XRPD spectrum including peaks at the diffraction angle (2θ±0.2°) of 8.9, 13.4, 14.1, 18.0, 19.8, 21.1, 21.7, 23.5, 25.7 and 32.7° when irradiated with a Cu-Kα light source. These peaks may be peaks with relative intensities of about 10% to 20% or more.

The above crystalline form may have chemical shifts (ppm±0.5 ppm) of 145.8, 157.8 and 164.5 ppm in the $^{13}$C CP/MAS TOSS solid state nuclear magnetic resonance (ssNMR) spectrum.

The above crystalline form may have an endothermic peak of the lowest point at about 151° C. and an endothermic peak at about 178° C. when running from a starting point of about 127° C., as measured by the DSC (10° C./min).

The above crystalline form may have a moisture content of about 3.2% (theoretical moisture content 3.30%) and a melting point of about 187-193° C.

The above crystalline form can be measured to have very low hygroscopic degree in a relative humidity range of 10-90% as measured by the DVS.

As another example, this patent document provides the crystalline anhydrous monohydrochloride (1 HCl) form of the compound of chemical formula (1).

The crystalline anhydrous monohydrochloride salt (1HCl) form of the compound of chemical formula (1) may have the XRPD spectrum including peaks at the diffraction angle (2θ±0.2°) of 9.5, 12.3, 13.0, 13.5, 14.2, 21.4, 23.0, 23.2, 23.5, 27.2 and 27.5° when irradiated with a Cu-Kα light source. These peaks may be peaks with relative intensities of about 10% to 20% or more.

The above crystalline form may have chemical shifts (ppm±0.5 ppm) of 148.9, 158.7 and 163.0 ppm in the $^{13}$C CP/MAS TOSS solid state nuclear magnetic resonance (ssNMR) spectrum.

The above crystalline form may have an endothermic peak of the lowest point at about 230° C. when running from a starting point of about 201° C., as measured by the DSC (10° C./min).

The above crystalline form may have a moisture content of about 0.1% and a melting point of about 238-243° C.

The above crystalline form can be measured to have very low hygroscopic degree in a relative humidity range of 10-90%, as measured by the DVS.

A general process for the preparation of crystalline forms (hydrate or anhydrous) of the compound of chemical formula (1) according to this patent document is provided. The process involves:

(a) providing a solution of the compound of chemical formula (1) in a solvent system (protic, aprotic or mixed);

(b) cooling the solution to effect formation of a crystal form (hydrate or anhydrous) of the compound of chemical formula (1); and (c) isolating the crystalline form (hydrate or anhydrous) of the compound of chemical formula (1).

A process for the preparation crystalline hydrochloride salt forms (hydrate or anhydrous) of the compound of chemical formula (1) is also provided. The process involves:

(a) providing a solution of the compound of chemical formula (1) in a solvent system (protic, aprotic or mixed);

(b) adding hydrochloric acid to the solution;

(c) cooling the solution to effect formation of a crystalline hydrochloride salt forms (hydrate or anhydrous) of the compound of chemical formula (1); and (d) isolating the crystalline hydrochloride salt form (hydrate or anhydrous) of the compound of chemical formula (1).

Non-limiting examples of the solvent systems are the following: acetone; acetonitrile; acetone/water; acetonitrile/water; ethanol; ethanol/water. DMSO; DMSO/water, DMF; DMF/water.

This process is highly-reproducible and the resulting crystalline product has good filterability.

The crystalline forms (hydrate or anhydrous) of the compound of chemical formula (1) according to this patent document and its crystalline hydrochloride salt forms (hydrate or anhydrous) do not require particular storage conditions and can be stably maintained for a long period of time. Capable of meeting the physicochemical properties required for pharmaceuticals including excellent solubility in water, they are readily usable in the manufacture of pharmaceutical compositions containing these as active ingredients.

The crystalline forms (hydrate or anhydrous) of the compound of chemical formula (1) according to this patent document have a high chemical purity, in some embodiments, the chemical purify is greater than about 75%, greater than about 80%, greater than about 85%, greater than about 90%, greater than about 95%, or greater than about 99%.

Pharmaceutical Composition

As disclosed in Korean Patent No. 1,013,319 and U.S. Pat. No. 8,003,658, incorporated herein in their entirety, it was proven that the compound of chemical formula (1) has an antiproliferative activity such as anticancer activity and has an activity of selectively and effectively inhibiting the growth and drug resistance of cancer ceils induced by tyrosine kinase or its variants.

In this respect, the crystalline form of the compound of chemical formula (1) and its hydrochloride salt can be used to produce a pharmaceutical composition for the treatment or prevention of various solid cancers, such as cancers or tumors, particularly lung cancer, breast cancer, etc. caused by tyrosine kinase or its variants.

The dosage of the crystalline form of the compound of chemical formula (1) and hydrochloride salts thereof may vary depending on the subject to be treated, the severity of the disease or condition, the rate of administration and the judgment of the prescribing physician, but they can be usually administered to an individual as an active ingredient in an amount of 1 to 2,000 mg per kg of body weight 70 kg of free base of the compound of chemical formula (1), preferably 5 to 1,000 mg based on the compound of chemical formula (1), usually on a schedule of one to four times a day, or on/off schedule, via an oral or parenteral route. In some cases, dosage less than the above-mentioned ranges may be more suitable, dosage more than the above-mentioned ranges may be also used without causing harmful side effects, and in the case of the higher dosage, it is administered in divided doses several times per day.

The pharmaceutical composition according to this patent document may be formulated according to the conventional method and may be prepared in various oral dosage forms such as tablets, pills, powders, capsules, syrups, emulsions or micro-emulsions, etc. or in parenteral dosage forms such as intramuscular, intravenous or subcutaneous administration.

When the pharmaceutical composition according to this patent document is prepared in the form of an oral formulation, examples of the carrier include cellulose, calcium silicate, corn starch, lactose, sucrose, dextrose, calcium phosphate, stearic acid, magnesium stearate, calcium stearate, gelatin, talc, surfactants, suspending agents, emulsifiers, diluents and the like. When the pharmaceutical composition according to this patent document is prepared in the form of an injection, examples of the carrier include water, saline solution, aqueous glucose solution, aqueous pseudosugar solution, alcohols, glycols, ethers (for example, polyethylene glycol 400), oils, fatty acids, fatty acid esters, glycerides, surfactants, suspending agents, emulsifiers and the like.

In some embodiments, the pharmaceutical composition further includes a non-metallic salt lubricant selected from the group consisting of glyceryl behenate, glyceryl palmitostearate, glyceryl monostearate, glyceryl trimyristate, glyceryl tristearate, sucrose fatty acid ester, palmitic acid, palmitoyl alcohol, stearic acid, stearyl alcohol, fumaric acid, polyethyleneglycol 4000, polyethyleneglycol 6000, polytetrafluoroethylene, starch, talc, hydrogenated castor oil, mineral oil, hydrogenated vegetable oil, silicon dioxide, and any combination thereof.

In some embodiments, the pharmaceutical composition further includes a metallic salt lubricant. Non-limiting examples include magnesium stearate, magnesium silicate, stearic acid, and calcium stearate.

A related aspect of the invention includes a kit for treating cancer including the crystalline form described herein or a pharmaceutical composition thereof. The kit or the pharmaceutical composition can contain an additional cytotoxic agent or a molecularly targeted agent. The crystalline form described herein or a pharmaceutical composition thereof and the additional cytotoxic agent can be administered sequentially or simultaneously, depending on the specific conditions of the subject.

A cytotoxic agent refers to an agent that has a cytotoxic effect on a ceil. A cytotoxic effect refers to the depletion, elimination and/or the killing of a target ceils (i.e., tumor cells). The cytotoxic agent may be at least one selected from the group consisting of an antimetabolite, a mitotic inhibitor, alkylating agent, a platinum-based antineoplastic drug, an mTOR inhibitor, a VEGF inhibitor, an aromatase inhibitor and a CDK4/6 inhibitor. The kit or combination of agents may include at least two cytotoxic agents. For example, the combination may include at least 2, at least 3, or at least 4 selected from the group consisting of an antimetabolite, a mitotic inhibitor, alkylating agent, a platinum-based antineoplastic drug, an mTOR inhibitor, a VEGF inhibitor, an aromatase inhibitor, a CDK4/8 inhibitor and ail of them.

The antimetabolite may be a drug that inhibits DNA synthesis in cells by suppressing formation of purines or pyrimidines, which are bases of a nucleotide. The antimetabolite may be selected from the group consisting of Capecitabine, 5-Fluorouracil, Gemcitabine, Pemetrexed, Methotrexate, 6-Mercaptopurine, Cladribine, Cytarabine, Doxifludine, Floxuridine, Fludarabine, Hydroxycarbamide, decarbazine, hydroxyurea, and asparaginase.

The mitotic inhibitor may be a microtubule-destabilizing agent, a microtubule-stabilizing agent, or a combination thereof. The mitotic inhibitor may be taxane, vinca alkaloid, epothilone, or a combination thereof.

The mitotic inhibitor may be selected from BT-062, HMN-214, eribulin mesylate, vindesine, EC-1089, EC-1458, EC-531, vintafolide, 2-methoxyestradiol, GTx-230, trastuzumab emtansine, crolibulin, D1302A-maytansinoid conjugates IMGN-529, lorvotuzumab mertansine, 8AR-3419, SAR-566858, IMP-03138, topotecan/vincristine combinations, BPH-8, fosbretabulin tromethamine, estramustine phosphate sodium, vincristine, vinflunine, vinorelbine, RX-21101, cabazitaxel, 8TA-9584, vinblastine, epothilone A, patupilone, ixabepilone, Epothilone D, paclitaxel, docetaxel, DJ-927, discodermolide, eleutherobin, and pharmaceutically acceptable salts thereof or combinations thereof.

As used herein, an "alkylating agent" is a substance that adds one or more alkyl groups (CnHm, where n and m are integers) to a nucleic acid, in the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine, chlorambucil, cyclophosphamide, bendamustine, ifosfamide, melphalan, melphalan flufenamine, and pharmaceutically acceptable salts thereof. Non-limiting examples of nitrosoureas include streptozocin, carmustine, lomustine, and pharmaceutically acceptable salts thereof. Non-limiting examples of alkyl sulfonates include busulfan and pharmaceutically acceptable salts thereof. Non-limiting examples of triazines include dacarbazine, temozolomide, and pharmaceutically acceptable salts thereof. Non-limiting examples of ethylenimines include thiotepa, altretamine, and pharmaceutically acceptable salts thereof. Other alkylating agents include ProLindac, Ac-225 BC-8, ALF-2111, trofosfamide, MDX-1203, thioureidobutyronitrile, mitobronitol, mitolactol, nimustine, glufosfamide, HuMax-TAC and PBD ADC combinations, BP-C1, treosulfan, nifurtimox, improsulfan tosilate, ranimustine, ND-01, HH-1, 22P1G ceils and ifosfamide combinations, estramustine phosphate, prednimustine, lurbinectedin, trabectedin, altreatamine, SGN-CD33A, fotemustine, nedaplatin, heptaplatin, apaziquone, SG-2000, TLK-58747, laromustine, procarbazine, and pharmaceutically acceptable salts thereof.

The platinum-based antineoplastic drug may be for example, Cisplatin, Carboplatin, Dicycloplatin, Eptaplatin, Lobaplatin, Miriplatin, Nedaplatin, Oxaliplatin, Picopiatin, or Satraplatin.

The term "mTOR inhibitors (mTOR inhibitor)" as used herein is used for purposes of a material to inhibit the mTOR signaling pathway of the conventional anticancer agents or immunosuppressive agents. The mTOR inhibitor may be rapamycin, temsirolimus, everolimus, ridaforolimus, MLN4924, XL388, GDG-0349, AZD2014, AZD8055, GSK105965, MLN0128 Ridaforolimus and the like.

"VEGF inhibitor" as used herein is any substance that decreases signaling by the VEGF-VEGFR pathway. VEGF inhibitors can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signaling pathway. Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what if would be in the same circumstance in the absence of the inhibitor.

Non-limiting examples of VEGF inhibitors include: (a) 4TBPPAPC or a closely related compound described in US2003/0125339 or U.S. Pat. No. 6,995,162 which is herein incorporated by reference in its entirety, particularly in parts disclosing 4TBPPAPC and closely related VEGF inhibitors; (b) AMG 706 or a closely related substituted alkylamine derivative described in US2003/0125339 or US2003/0225106 or U.S. Pat. No. 6,995,162 or 6,878,714 each of which is herein incorporated by reference in its entirety, particularly in parts disclosing AMG 706 and these closely related VEGF inhibitors; (c) Avastin™ or a closely related non-naturally occurring humanized monoclonal antibody that binds to VEGF, is a VEGF inhibitor, and is at least 90% identical in sequence to Avastin™; (d) Nexavar® or a closely related substituted omega-carboxyaryl diphenyl urea or derivative thereof described in WO00/42012, WO00/41698, US2005/0038080A1, US2003/0125359A1, US2002/0165394A1, US2001/003447A1, US2001/0016659A1, and US2002/013774A1 which are herein incorporated by reference in their entirety, particularly in parts disclosing these VEGF inhibitors; (e) PTK/ZK or a closely related anilinophthalazine or derivative thereof that binds to and inhibits the activity of multiple receptor tyrosine kinases including binding to the protein kinase domain and inhibition of VEGFR1 and VEGFR2; (f) Sutent® or a closely related derivative of (5-[5-fluoro-2-oxo-1,2-dihydroindol-(3Z)-ylidenemethyl]-2,4-dimethyl-1H-pyrrole-3-carboxylic acid [2-diethylaminoethyl]amide) that is a VEGF inhibitor; and (g) VEGFinhibitors as described in US2006/0241115, including those of Formula IV therein.

Further examples of VEGF inhibitors are the following: (a) 4TBPPAPC, as described in US2003/0125339 or U.S. Pat. No. 6,995,162 which is herein incorporated by reference in its entirety, particularly in parts disclosing 4TBPPAPC; (b) AMG 706, as described in US2003/0125339 or U.S. Pat. No. 6,995,162 or 6,878,714 which is herein incorporated by reference in its entirety, particularly in parts disclosing AMG 706; (c) Avastin™; (d) Nexavar®, as described in WO00/42012, WO00/41698, US2005/0038080A1, US2003/0125359A1, US2002/0165394A1, US2001/003447A1, US2001/0016659A1, and US2002/013774A1 which are herein incorporated by reference in their entirety, particularly in parts disclosing Nexavar®; (e) PTK/ZK; (f) Sutent®, and (g) VEGF inhibitors of Formula IV as described in US2006/0241115.

In some embodiments, the VEGF inhibitor is pegaptanib. In one embodiment, the VEGF inhibitor is bevacizumab. In one embodiment, the VEGF inhibitor is ranibizumab. In one embodiment, the VEGF inhibitor is lapatinib. In one embodiment, the VEGF inhibitor is sorafenib. In one embodiment, the VEGFinhibitor is sunitinib. In one embodiment, the VEGF inhibitor is axitinib. In one embodiment, the VEGF inhibitor is pazopanib. In one embodiment, the VEGFinhibitor is aflibercept.

By "aromatase inhibitor" it is meant non-steroidal and steroidal compounds that inhibit the enzyme aromatase thereby preventing the conversion of androgens to estrogens, preferably those which inhibit aromatase activity in vitro with an IC50 value of less than 10~5 M as well as their pharmaceutically acceptable salts. Exemplary aromatase inhibitors for use in the methods herein described include without limitation anastrozole, letrozole, exemestane, vorozole, formestane, fadrozole, aminoglutethimide, testolactone, 4-hydroxyandrostenedione, I,4,6-androstatrien-3,17-dione and 4-androstene-3,6,17-trione.

The terms "cyclin dependent kinase 4/6 inhibitor" and "CDK4/6 inhibitor" as used herein refer to a compound that selectively targets, decreases, or inhibits at least one activity of CDK4 and/or CDK6. Non-limiting examples of inhibitors of CDK4/6 include Abemaciclib (LY2835219), palbociclib (PD0332991), LEE-011 (ribociclib), LY2835219 (abemaciclib), G1T28-1, SHR6390, or P276-00, or a derivative of any one of palbociclib, LEE-011, G1T28-1, SHR6390, or P276-00. In certain embodiments, the CDK4/6 inhibitor may be derived from pyridopyrimidine, pyrrolopyrimidine or indolocarbazole compounds.

As used herein, a "molecularly targeted agent" is a substance that interferes with the function of a single molecule or group of molecules, preferably those that are involved in tumor growth and progression, when administered to a subject. Non-limiting examples of molecularly targeted agent of this patent document include signal transduction inhibitors, modulators of gene expression and other cellular functions, immune system modulators, antibody-drug conjugates (ADCs), and combinations thereof.

The molecularly targeted agent may be selected from epidermal growth factor receptor family inhibitors (EGFRi), mammalian target of rapamycin (mTor) inhibitors, immune checkpoint inhibitors, anaplastic lymphoma kinase (ALK) inhibitors, B-cell lymphoma-2 (BCL-2) inhibitors, B-Raf inhibitors, cyclin-dependent kinase inhibitors (CDKi), ERK inhibitors, histone deacetylase inhibitors (HDACi), heat shock protein-90 inhibitors (HSP90i), Janus kinase inhibitors, mitogen activated protein kinase (MAPK) inhibitors, MEK inhibitors, poly ADP ribose polymerase (PARP) inhibitors, phosphoinositide 3-kinase inhibitors (PI3Ki), Ras inhibitors, and combinations thereof.

The molecularly targeted agent may be selected from ado-trastuzumab emtansine, alemtuzumab, cetuximab, ipilimumab, ofatumumab, panitumumab, pertuzumab, rituximab, tositumomab, 131I-tositumomab, trastuzumab, brentuximab vedotin, denileukin diftitox, ibritumomab tiuxetan, axitinib, bortezomib, bosutinib, cabozantinib, crizotinib, carfilzomib, dasatinib, erlotinib, gefitinib, imatinib mesylate, lapatinib, nilotinib, pazopanib, ponatinib, regorafenib, ruxolitinib, sorafenib, sunitinib, tofacitinib, vandetanib, vemurafenib, alitretinoin, bexarotene, everolimus, romidepsin, temsirolimus, tretinoin, vorinostat, and pharmaceutically acceptable salts thereof or combinations thereof. The molecularly targeted agent may include an antibody or an antibody moiety.

The EGFRi may be selected from erlotinib, gefitinib, lapatinib, canetinib, pelitinib, neratinib, (R,E)-N-(7-chloro-1-(1-(4-(dimethylamino)but-2-enoyl)azepan-3-yl)-1H-benzo[d]imidazol-2-yl)-2-methylisonicotinamide, Trastuzumab, Margetuximab, panitumumab, matuzumab, Necitumumab, pertuzumab, nimotuzumab, zalutumumab, Necitumumab, cetuximab, icotinib, afatinib, and pharmaceutically acceptable salt thereof. The molecularly targeted agent may be an anti-EGFR family antibody or a complex including the anti-EGFR family antibody. The anti-EGFR family antibody may be an anti-HER1 antibody, an anti-HER2 antibody, or an anti-HER4 antibody.

Method of Treating Cancer

Another aspect of the invention provides a method of treating a neoplasm in a subject comprising administering to a subject in need thereof the novel crystalline form described herein, the pharmaceutical composition thereof, a combination with one or more agents, or a kit containing the novel crystalline form.

Non-limiting examples of the neoplasm that can be treated according to this patent document include lung cancer including non-small cell lung cancer, breast cancer, stomach cancer, colon cancer, pancreatic cancer, prostate cancer, myeloma, head and neck cancer, ovarian cancer, esophageal cancer, or metastatic cell carcinoma. In some embodiments, the neoplasm associated with overexpression or amplification of at least one gene of HER1, HER2, and HER4 or a mutant thereof may be an abnormal growth of tissue, which if it forms a mass, is commonly referred to as a tumor having overexpression of at least one of HER1, HER2, HER4 and mutant thereof or amplification of at least one gene coding of HER1, HER2, HER4 or mutant thereof. The mutant may be HER1 having exon 19 deletion, T790M substitution, L828R substitution, or combination thereof. As used herein, "overexpression" indicates that the protein is expressed at a higher level than normal cells. The expression level can be measured using immunohistochemistry, fluorescence in situ hybridization (FISH), or chromogenic in situ hybridization (CISH).

The term "wild type" as used herein is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Neoplasm including cancers that are either wild type or mutant for HER1, HER2, or HER4 or have amplification of HER1, HER2, or HER4 genes or have over expression of HER1, HER2, or HER4 protein are identified by known methods.

For example, wild type or mutant HER1, HER2, and HER4 tumor cells can be identified by DNA amplification and sequencing techniques, DNA and RNA detection techniques, including, but not limited to Northern and Southern blot, respectively, and/or various biochip and array technologies or in-situ hybridization.

Wild type and mutant polypeptides can be detected by a variety of techniques including, but not limited to immunodiagnostic techniques such as ELISA, Western blot or immunocytochemistry.

The cancer to be treated may be associated with EGFR and/or HER2 exon 20 mutations, such as exon 20 insertion mutations. For instance, the novel crystalline form of the compound of this patent document or its combination with one or more agents can be used for the treatment of NSCLC patients with EGFR exon 20 mutations.

In some aspects, the cancer to be treated with the novel crystalline form of the compound of this patent document or its combination with one or more agents is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

The administration of a therapeutically effective amount of the novel crystalline form of compound of Formula (1) or its combinations with other agents are advantageous over many other conventional therapies including: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, vi) an increase in the bioavailability of one or both of the component compounds, or vii) an increase in apoptosis over the individual component compounds.

In some embodiments, the kit or combination of the novel crystalline form of the compound of Formula (1) of this patent document may include poziotinib and an anti-EGFR family antibody. The anti-EGFR family antibody may be trastuzumab, cetuximab, margetuximab, matuzumab, panitumumab, necitumumab, or pertuzumab. An example of the combination may be poziotinib and trastuzumab; or poziotinib and cetuximab. Poziotinib may be hydrochloride. The combination may further include a cytotoxic agent. The cytotoxic agent may be a mitotic inhibitor. The mitotic inhibitor may be taxane, vinca alkaloid, epothilone, or a combination thereof. The vinca alkaloid may be at least one drug selected from the group consisting of vinblastine, vincristine, vindesine and vinorelbine. An example of the combination may include poziotinib; and trastuzumab and vinorelbine. The vinorelbine may be in the form of an injection. The taxane may be paclitaxel or docetaxel. An example of the combination may include poziotinib; and cetuximab and pacliataxel. The paclitaxel may be in the form of an injection.

The novel crystalline form of the compound of Formula (1) of this patent document may be administered in an amount of 0.1 mg to 50 mg. Trastuzumab may be administered in an amount of 0.5 mg to 10 mg per kg of a body weight. Cetuximab may be administered in an amount of from 100 mg/m2 to 500 mg/m2 of a surface area of the body.

Vinorelbine may be administered in an amount of 0.5 mg/m2 to 50 mg/m2 of a surface area of the body. Also, paclitaxel may be administered in an amount of 100 mg/m2 to 300 mg/m2 of a surface area of the body.

Trastuzumab, sold under the brand name Herceptin™ among others, is a monoclonal antibody used to treat breast cancer. Specifically it is used for breast cancer that is HER2 receptor positive. Trastuzumab is given by slow injection into a vein and injection just under the skin.

Cetuximab is an epidermal growth factor receptor (EGFR) inhibitor used for the treatment of metastatic colorectal cancer, metastatic non-small cell lung cancer and head and neck cancer. Cetuximab is a chimeric (mouse/human) monoclonal antibody given by intravenous infusion that is distributed under the trade name Erbitux in the U.S. and Canada by the drug company Bristol-Myers Squibb and outside the U.S. and Canada by the drug company Merck KGaA. In Japan, Merck KGaA, Bristol-Myers Squibb and Eli Lilly have a co-distribution.

Paclitaxel (PTX), sold under the brand name Taxol among others, is a chemotherapy medication used to treat a number of types of cancer. This includes ovarian cancer, breast cancer, lung cancer, Kaposi sarcoma, cervical cancer, and pancreatic cancer. It is given by injection into a vein.

In one embodiment, the kit/combination may include the novel crystalline form of the compound of Formula (1) of this patent document and a mitotic inhibitor. The mitotic inhibitor may be selected from BT-062, HMN-214, eribulin mesylate, vindesine, EC-1069, EC-1456, EC-531, vintafolide, 2-methoxyestradiol, GTx-230, trastuzumab emtansine, crolibulin, D1302A-maytansinoid conjugates, IMGN-529, lorvotuzumab mertansine, SAR-3419, SAR-566658, IMP-03138, topotecan/vincristine combinations, BPH-8, fosbretabulin tromethamine, estramustine phosphate sodium, vincristine, vinflunine, vinorelbine, RX-21101, cabazitaxel, STA-9584, vinblastine, epothilone A, patupilone, ixabepilone, Epothilone D, paclitaxel, docetaxel, DJ-927, discodermolide, eleutherobin, and pharmaceutically acceptable salts thereof or combinations thereof. An example of the combination may include poziotinib and taxane, vinca alkaloid, or a combination thereof. The vinca alkaloid may be at least one drug selected from the group consisting of vinblastine, vincristine, vindesine and vinorelbine. The taxane may be paclitaxel or docetaxel. An example of the combination may include poziotinib and pacliataxel; or poziotinib and vinorelbine. The neoplasm may be a breast cancer in which Her2 is overexpressed.

Poziotinib may be administered in an amount of 0.1 mg to 50 mg. Also, vinorelbine may be administered in an amount of 0.5 mg/m2 to 50 mg/m2 of a surface area of the body. Also, paclitaxel may be administered in an amount of from 100 mg/m2 to 300 mg/m2 of a surface area of the body.

Vinorelbine (NVB), sold under the brand name Navelbine among others, is a chemotherapy medication used to treat a number of types of cancer. This includes breast cancer and non-small cell lung cancer. It is given by injection into a vein or by mouth. Vinorelbine is in the vinca alkaloid family of medications. It is believed to work by disrupting the normal function of microtubules and thereby stopping cell division.

In one embodiment, the combination may include the novel crystalline form of the compound of Formula (1) of this patent document and an mTOR inhibitor. The mTOR inhibitor may be selected from zotarolimus, umirolimus, temsirolimus, sirolimus, sirolimus NanoCrystal, sirolimus TransDerm, sirolimus-PNP, everolimus, biolimus A9, ridaforolimus, rapamycin, TCD-10023, DE-109, MS-R001, MS-R002, MS-R003, Perceiva, XL-765, quinacrine, PKI-587, PF-04691502, GDC-0980, dactolisib, CC-223, PWT-33597, P-7170, LY-3023414, INK-128, GDC-0084, DS-7423, DS-3078, CC-115, CBLC-137, AZD-2014, X-480, X-414, EC-0371, VS-5584, PQR-401, PQR-316, PQR-311, PQR-309, PF-06465603, NV-128, nPT-MTOR, BC-210, WAY-600, WYE-354, WYE-687, LOR-220, HMPL-518, GNE-317, EC-0565, CC-214, ABTL-0812, and pharmaceutically acceptable salts thereof or combinations thereof. An example of the combination may include poziotinib and rapamycin. The rapamycin may be in the form of an injection. Rapamycin, also known as sirolimus, is a compound produced by the bacterium *Streptomyces hygroscopicus*.

The novel crystalline form of the compound of Formula (1) of this patent document may be administered in an amount of 0.1 mg to 50 mg. Also, rapamycin may be administered in an amount of 0.5 mg/m2 to 10 mg/m2 of a surface area of the body.

In one embodiment, the kit/combination may include the novel crystalline form of the compound of Formula (1) of this patent document and antimetabolite. The antimetabolite may be selected from the group consisting of capecitabine, 5-fluorouracil, gemcitabine, pemetrexed, methotrexate, 6-mercaptopurine, cladribine, cytarabine, doxifludine, floxuridine, fludarabine, hydroxycarbamide, decarbazine, hydroxyurea, and asparaginase. An example of the combination may include poziotinib and 5-fluorouracil. The 5-fluorouracil may be in the form of an injection.

The novel crystalline form of the compound of Formula (1) of this patent document may be administered in an amount of 0.1 mg to 50 mg. 5-Fluorouracil may be administered in an amount of 100 mg/m2 to 3,000 mg/m2 of a surface area of the body.

Fluorouracil (5-FU), sold under the brand name Adrucil among others, is a medication used to treat cancer. By injection into a vein it is used for colon cancer, esophageal cancer, stomach cancer, pancreatic cancer, breast cancer, and cervical cancer.[2] As a cream it is used for basal cell carcinoma. Fluorouracil is in the antimetabolite and pyrimidine analog families of medications. How it works is not entirely clear but believed to involve blocking the action of thymidylate synthase and thus stopping the production of DNA.

In one embodiment, the kit/combination may include the novel crystalline form of the compound of Formula (1) of this patent document and a platinum-based antineoplastic drug. The platinum-based antineoplastic drug may be selected from the group consisting of cisplatin, carboplatin, dicycloplatin, eptaplatin, lobaplatin, miriplatin, nedaplatin, oxaliplatin, picoplatin, and satraplatin. An example of the combination may include poziotinib and cisplatin. The cisplatin may be in the form of an injection.

Poziotinib may be administered in an amount of 0.1 mg to 50 mg. Cisplatin may be administered in an amount of 1 mg/m2 to 100 mg/m2 of a surface area of the body.

Cisplatin is a chemotherapy medication used to treat a number of cancers. This includes testicular cancer, ovarian cancer, cervical cancer, breast cancer, bladder cancer, head and neck cancer, esophageal cancer, lung cancer, mesothelioma, brain tumors and neuroblastoma. It is used by injection into a vein. Cisplatin is in the platinum-based antineoplastic family of medications. It works in part by binding to, and inhibiting DNA replication.

Pharmaceutical formulations or agents in a kit may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

The novel crystalline forms or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

Hereinafter, this patent document will be described with reference to specific examples. However, the following embodiments are only illustrative of the present invention, and the scope of this patent document is not limited thereto.

Analytical Instruments and Measuring Methods

1. X-Ray Powder Diffraction (XRPD)

X-ray Powder Diffraction (XRPD) spectroscopy was conducted on the D8 Advance (Bruker ASX, Germany) analyzer from 3°2θ to 40° 2θ for the sample. When the amount of the sample is <100 mg, about 5-10 mg of the sample is gently squeezed onto the glass slide fitted to the sample holder. When the amount of sample was >100 mg, about 100 mg of sample was gently squeezed onto the plastic sample holder so that sample surface was smooth and was just above the sample holder level.

The measurements were made as follows:

Anode material (Kα): Cu Kα (1.54056A)
Scan range: 3-40 degrees
Generator settings: 100 mA, 40.0 kV
Scan speed: 1 sec/step
Divergent slit size (Diver slit): 0.3 degree
Anti-scatter slit: 0.3 degree
Temperature: 20° C.
Step size: 0.02 deg 2θ
Rotating: Use
Goniometer radius: 435 mm 2. Differential Scanning Calorimetry (DSC)

Differential Scanning Calorimeter (DSC) analysis was conducted on the STA-1000 (Scinco, Korea) analyzer at 30-350° C. 5-10 mg of sample was weighed into the aluminum DSC pan and sealed non-hermetically with the perforated aluminum lid, and then the heat flow reaction (DSC) generated by heating the sample from 30° C. to 350° C. at a scan rate of 10° C./min was monitored.

3. Dynamic Vapor Sorption (DVS)

Dynamic Vapor Sorption (DVS) analysis was conducted on the DVS advantage (Surface measurement system, United Kingdom) analyzer at 25° C. and relative humidity of 0-90%.

10 mg of sample was placed in the wire mesh steam sorption balance pan and attached to the DVS-advantage dynamic vapor adsorption balance by the Surface Measurement Systems. The sample was applied to ramping profile of relative humidity (RH) of 10-90% in 10% increments while maintaining the sample in each step until a stable weight was achieved (99.5% step completion). After the completion of the sorption cycle, the sample was dried using the same procedure, during which the relative humidity was returned to a relative humidity below 0% all the time. The change in weight during the sorption/desorption cycle (repetition of 3 times) was recorded to determine the hygroscopicity of the sample.

4. Solid State Nuclear Magnetic Resonance (ssNMR)

For the purpose of comparing crystalline polymorphs in solid state using the nuclear magnetic resonance spectrometer, the solid state nuclear magnetic resonance (ssNMR) analysis was conducted at room temperature using a Bruker Avance II 500 MHz Solid NMR system (Bruker, Germany) analyzer after placing 100 mg of sample in the 4 mm sample tube. The analysis conditions of the $^{13}$C NMR spectra ($^{13}$C CP/MAS TOSS ssNMR) are as follows.

Frequency: 125.76 MHz
Spectrum width: 20 kHz
Sample rotation speed at magic angle: 5 kHz
Pulse sequence: CP (Cross Polarization) SPINAL 64 with decoupling
(Decoupling power of 80 kHz)
Repetition delay: 5 seconds
Contact time: 2 ms
Number of scans: 4096
External standard: adamantane 5. High Performance Liquid Chromatography (HPLC)

High performance liquid chromatography (HPLC) was conducted on the Agilent 1100/1200 series HPLC Systems (Agilent, USA) analyzer for the purpose of purity and content analysis including stability test and the like. The analysis conditions of the HPLC are as follows.

Conditions of purity and content analysis: Thienopyrimidine compound of chemical formula (1)
Column: Hydrosphere C18 (YMC), 5 μm (150 mm×4.6 mm)
Column temperature: 30° C.
Detector: Ultraviolet absorptiometer
Detection wavelength: 254 nm
Flow rate: 1.0 mL/min
Analysis time: 35 minutes
Eluent: $NaClO_4$—$NaH_2PO_4$-phosphate buffer solution (pH 2.5±10.1)/$CH_3CN$=40/60 (v/v %)

6. Ion Chromatography (IC)

Ion Chromatograph (IC) analysis was conducted on the Thermo Fisher Scientific ICS-2500 series IC Systems (Thermo Fisher Scientific, USA) analyzer for the purpose of content analysis of hydrochloric acid in the hydrochloride salt. The analysis conditions of the IC are as follows.

Conditions of Content Analysis: Thienopyrimidine Compound of Chemical Formula (1)
Column: IonPac AS19 (Dionex), (250 mm×4 mm), Guard (50 mm×4 mm)
Column temperature: 30° C.
Detector: Electrical Conductivity Detector (CD)
Suppressor: ASRS 4 mm, current 40 mA
Flow rate: 1.0 ml/min
Analysis time: 30 minutes
Eluent: 10 mM potassium hydroxide solution 7. Moisture Measurement Moisture measurement was conducted using the 795KFT Titrino (Metrohm, Switzerland) Karl-Fischer moisture analyzer.

8. Melting Point Measurement

Melting point measurement was conducted using the IA9200 (Electrothermal, UK) melting point apparatus.

Reference Example: Preparation of the Compounds of Chemical Formula (1)

100 g of the compound of chemical formula (1) prepared according to the method of Korean Patent Registration No. 1,013,319 and U.S. Pat. No. 8,003,658 cited in the present specification or a similar method was dissolved in the mixed solution of 300 ml of dichloromethane and 300 ml of methanol, stirred at 40° C. for 30 minutes, and the insoluble solid was filtered out using a filter paper. Distillation under reduced pressure gave 93 g (yield 93%) of the title compound.

Moisture content: 2.1%
Analysis of Characteristics

Figure 1F:
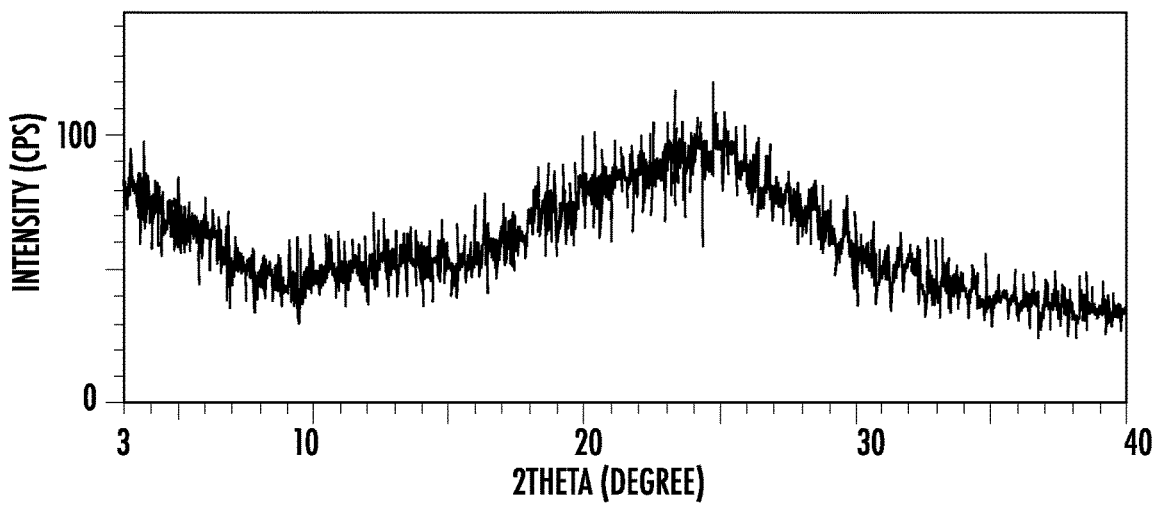
FIGS. 1F and 1G show the XRPD spectrums of the compound of chemical formula (1) and its amorphous hydrochloride salt form according to the comparative example.
Figure 1G:
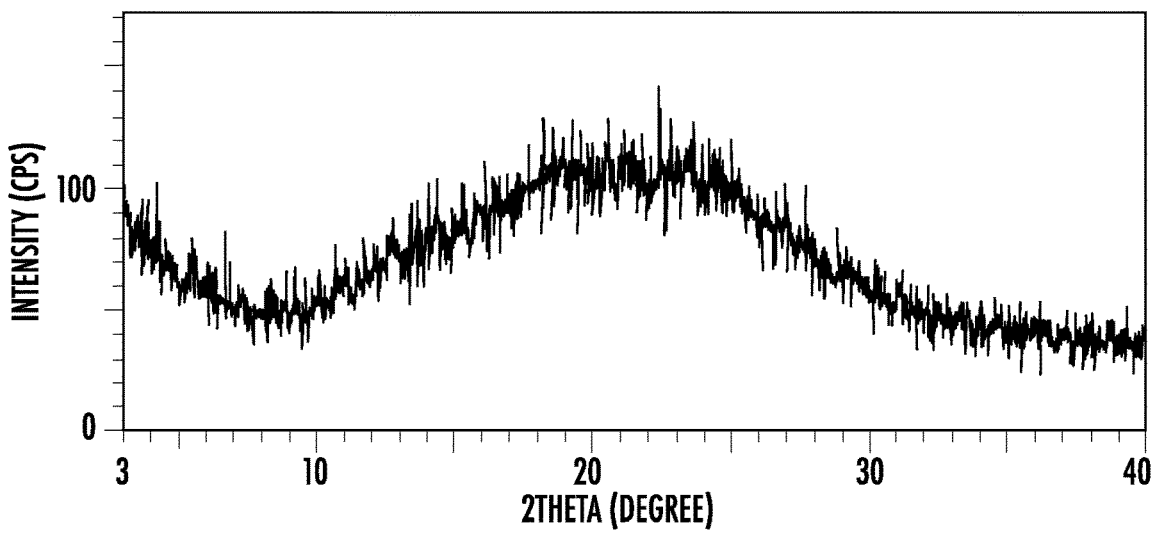
Figure 2A:
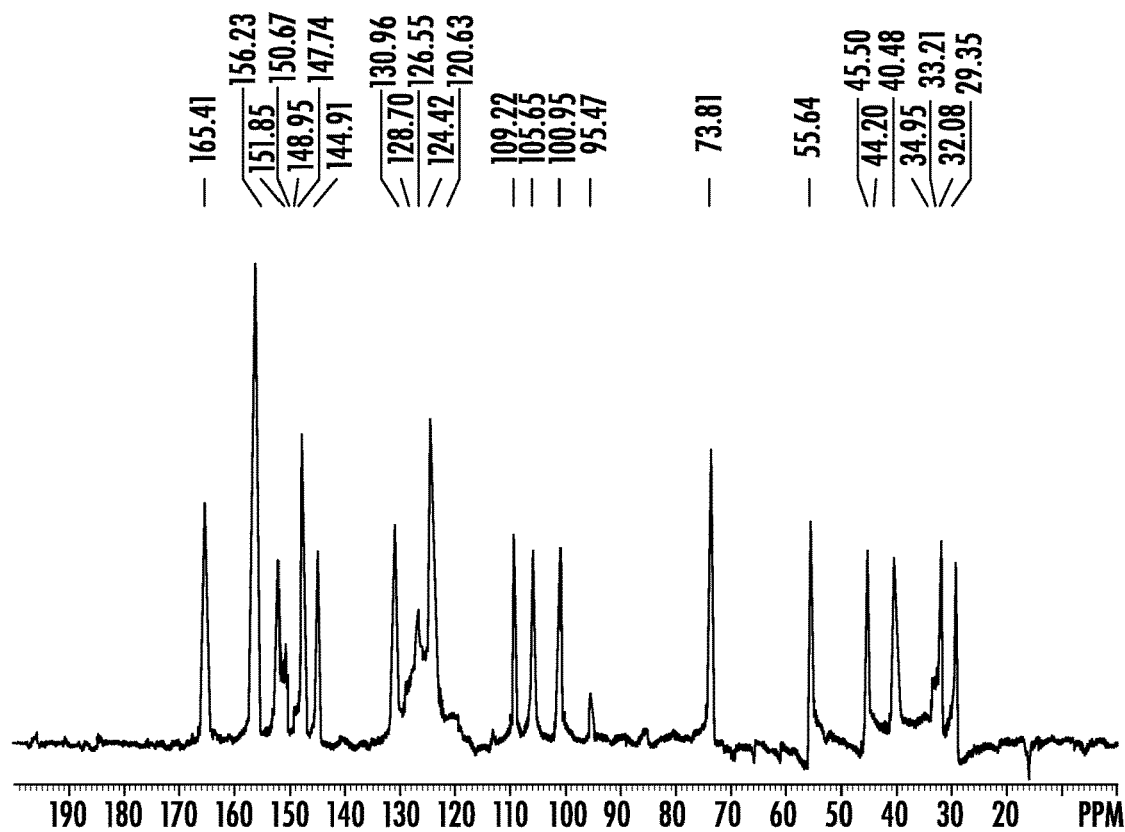
FIGS. 2A, 2B, 2C, 2D and 2E show the solid state nuclear magnetic resonance (ssNMR) spectrums of the compound of chemical formula (1) and its crystalline hydrochloride salt form according to the example.
Figure 2B:
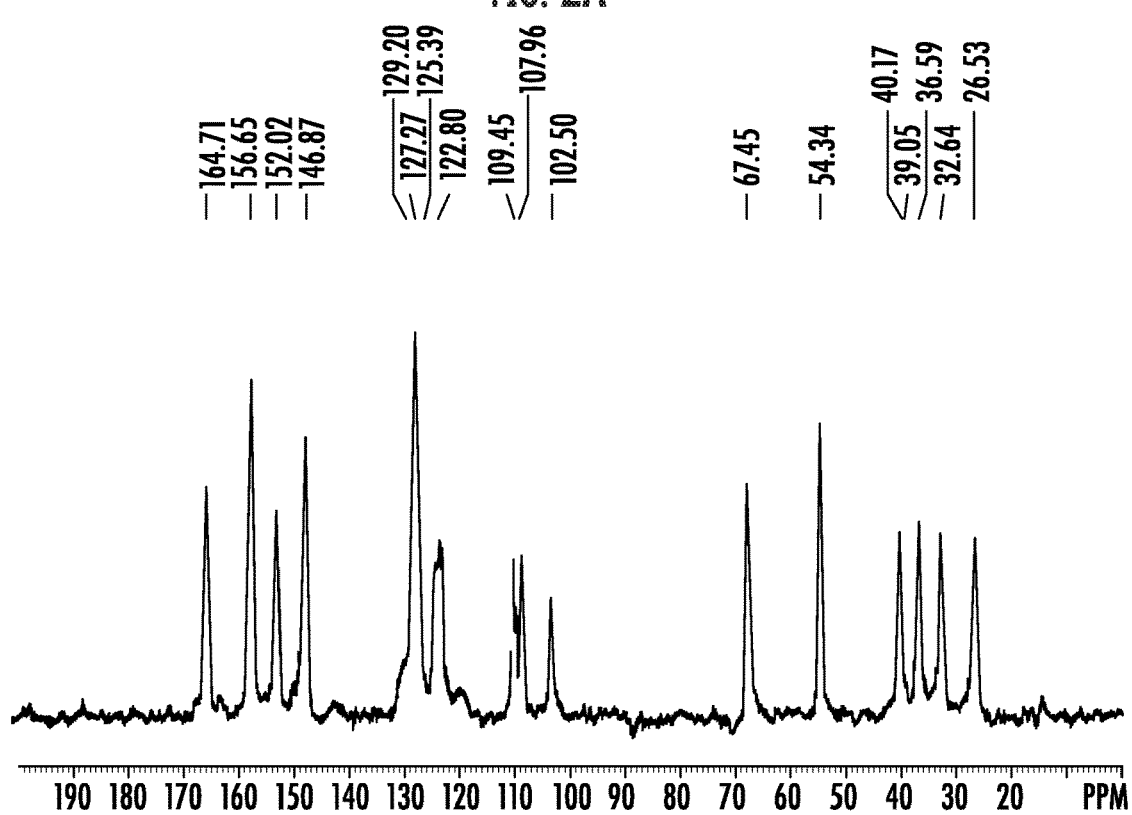
Figure 2C:
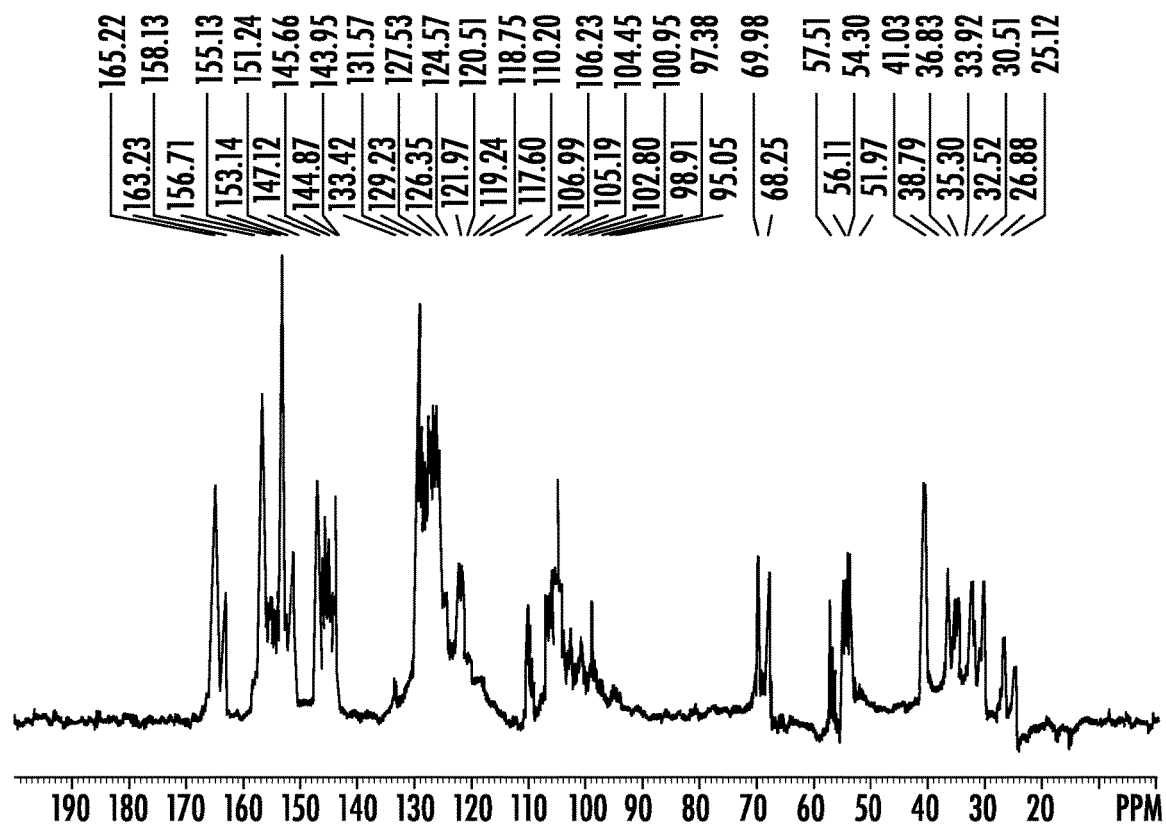
Figure 2D:
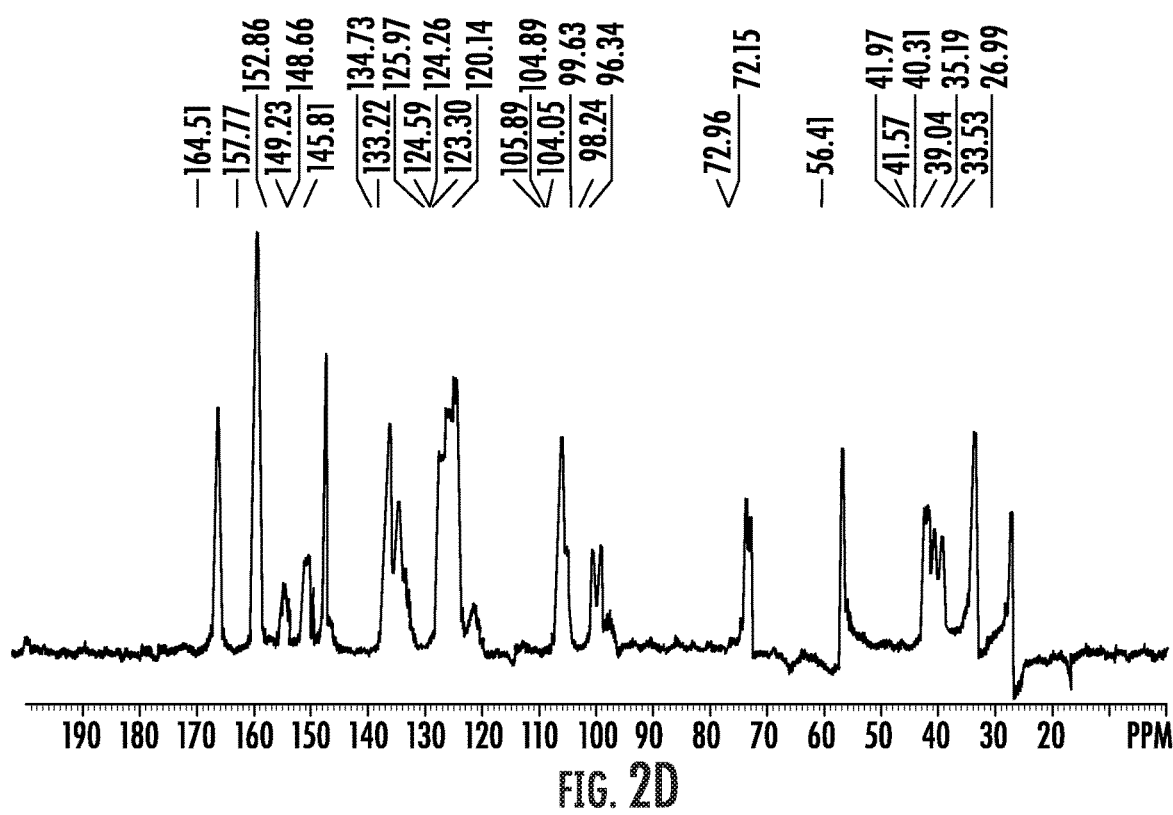
Figure 2E:
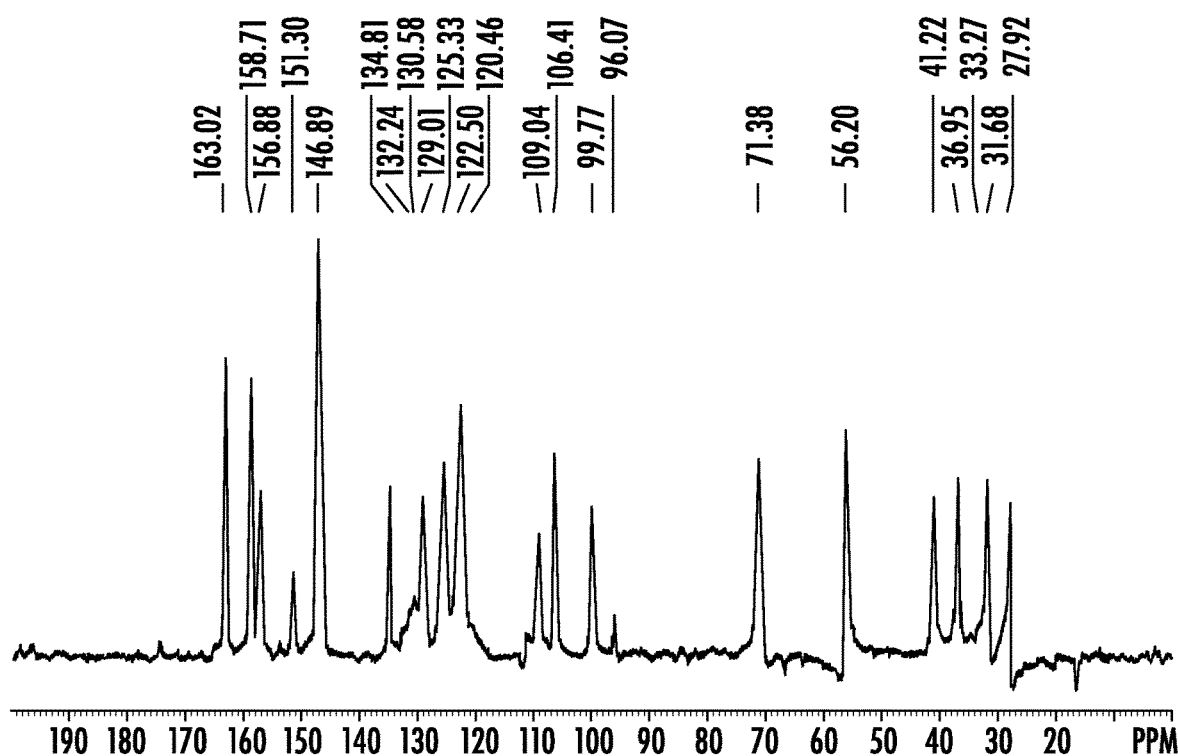
Figure 2F:
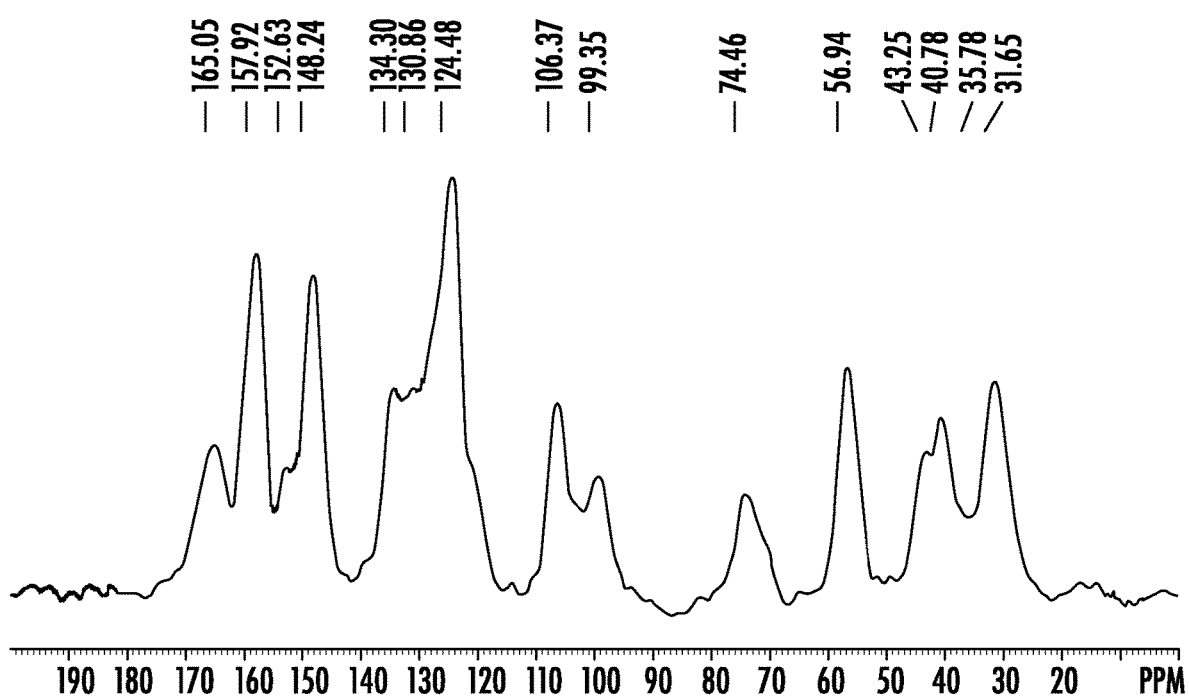
FIGS. 2F and 2G show the ssNMR spectrums of the compound of chemical formula (1) and its amorphous hydrochloride salt form according to the comparative example.
Figure 2G:
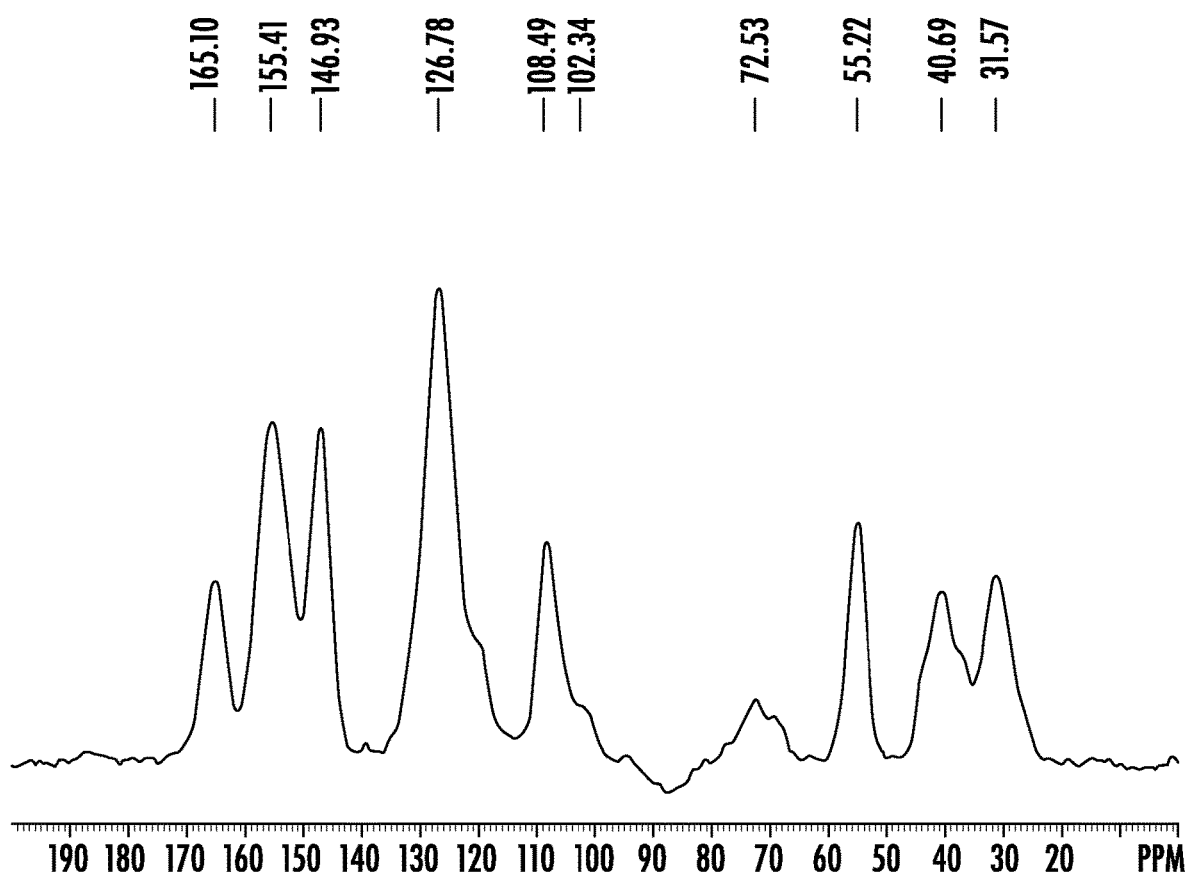
Figure 3A:
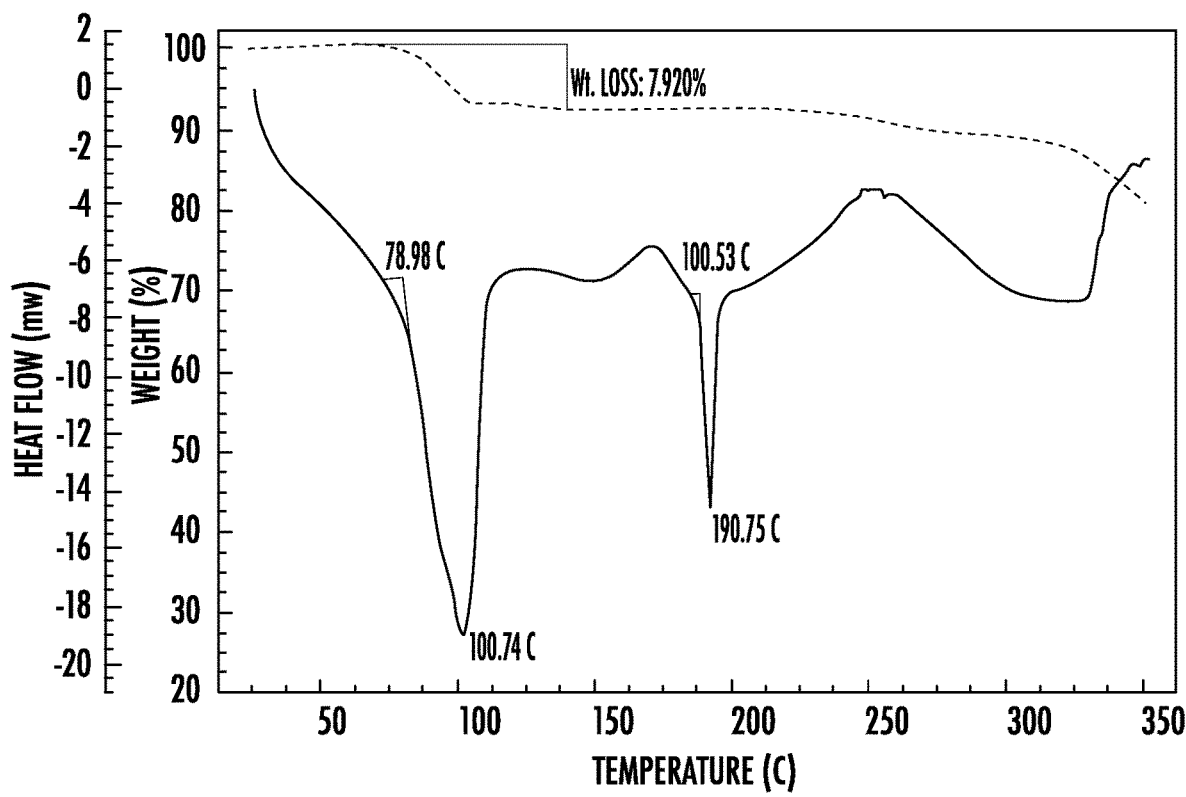
Figure 3B:
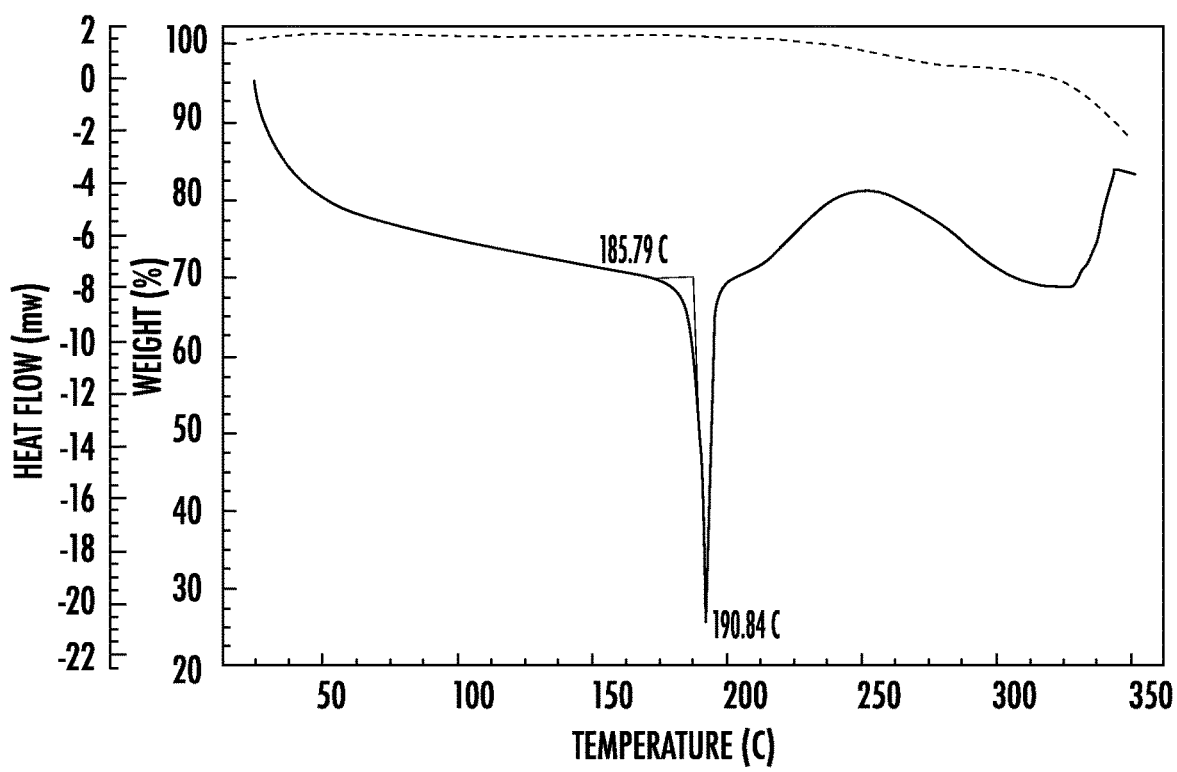
Figure 3C:
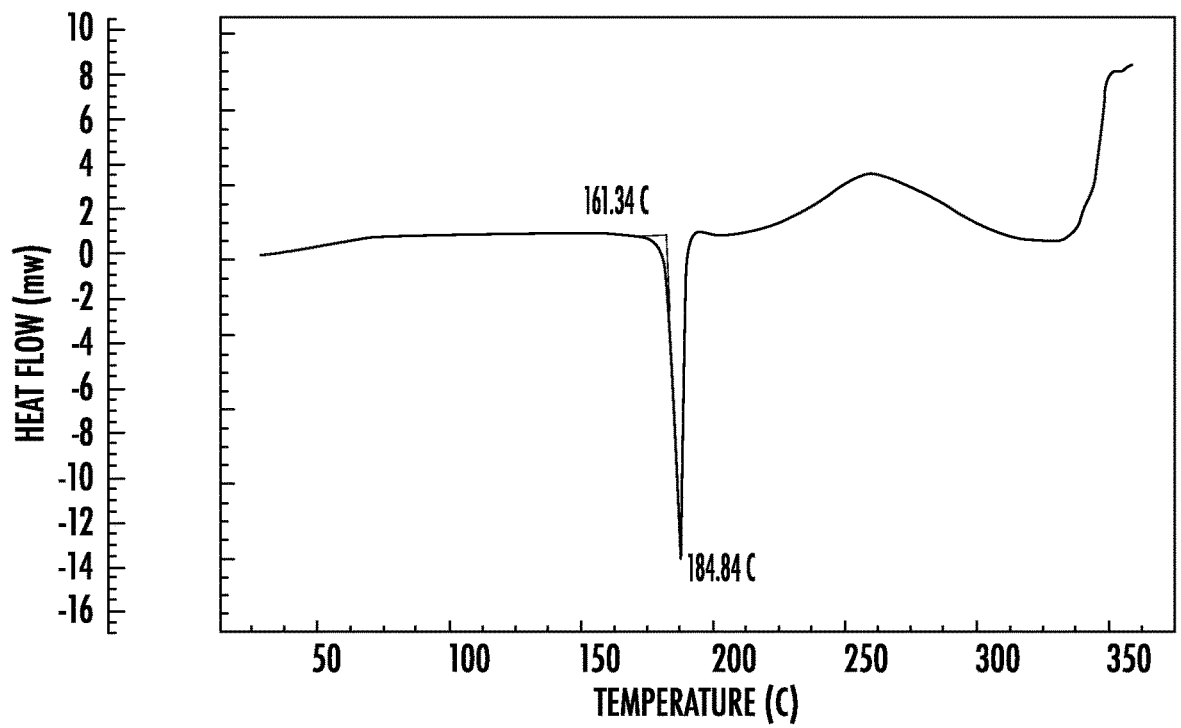
FIG. 3C shows DSC for the crystalline form prepared in Example 3.
Figure 3D:
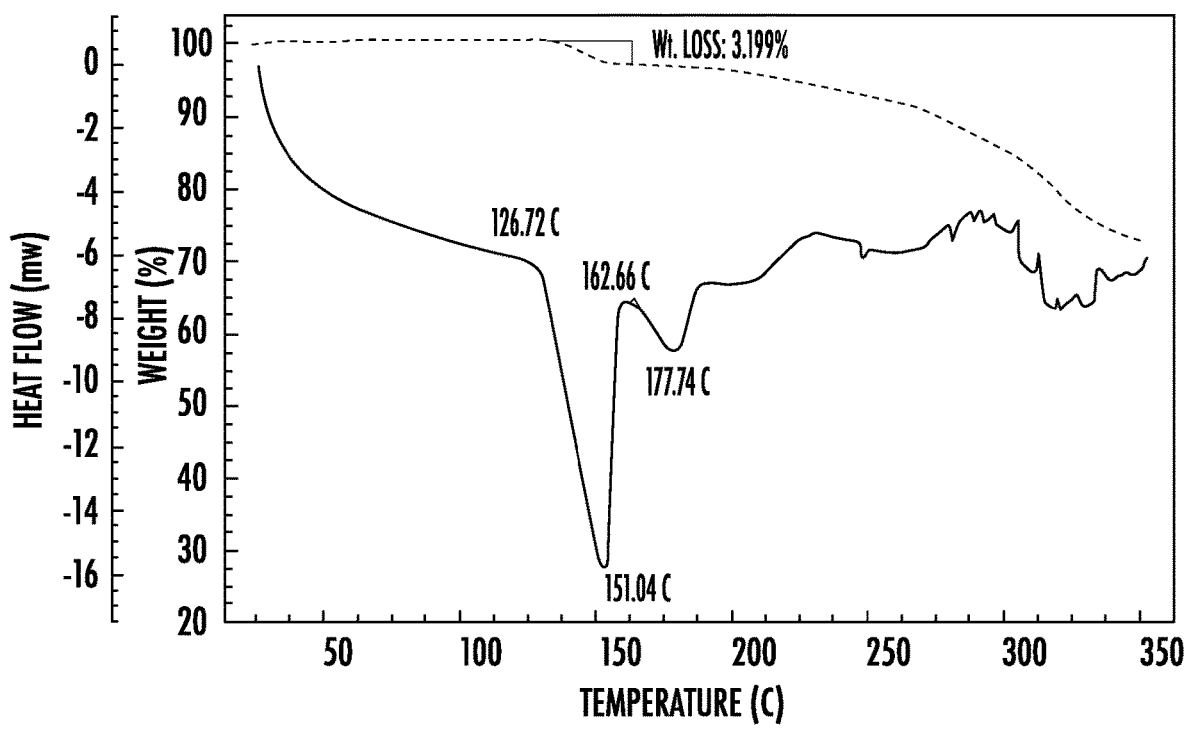
Figure 3E:
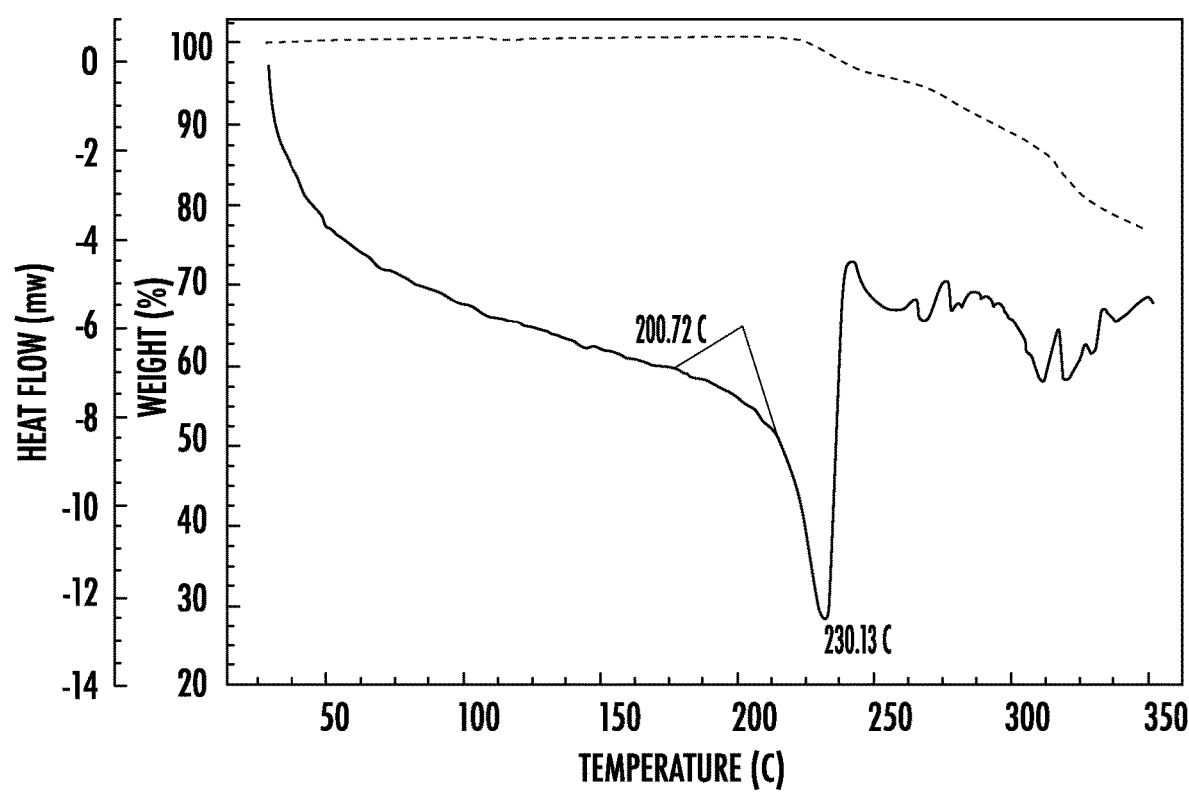
Figure 4A:
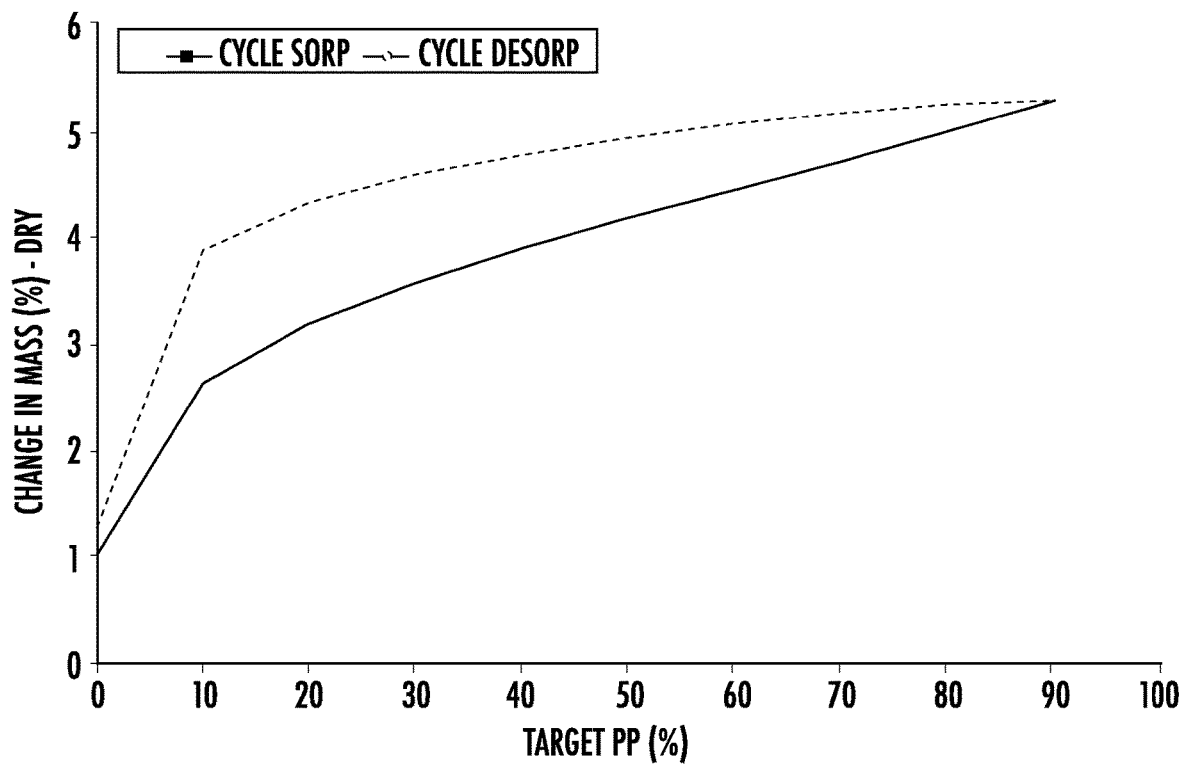
Figure 4B:
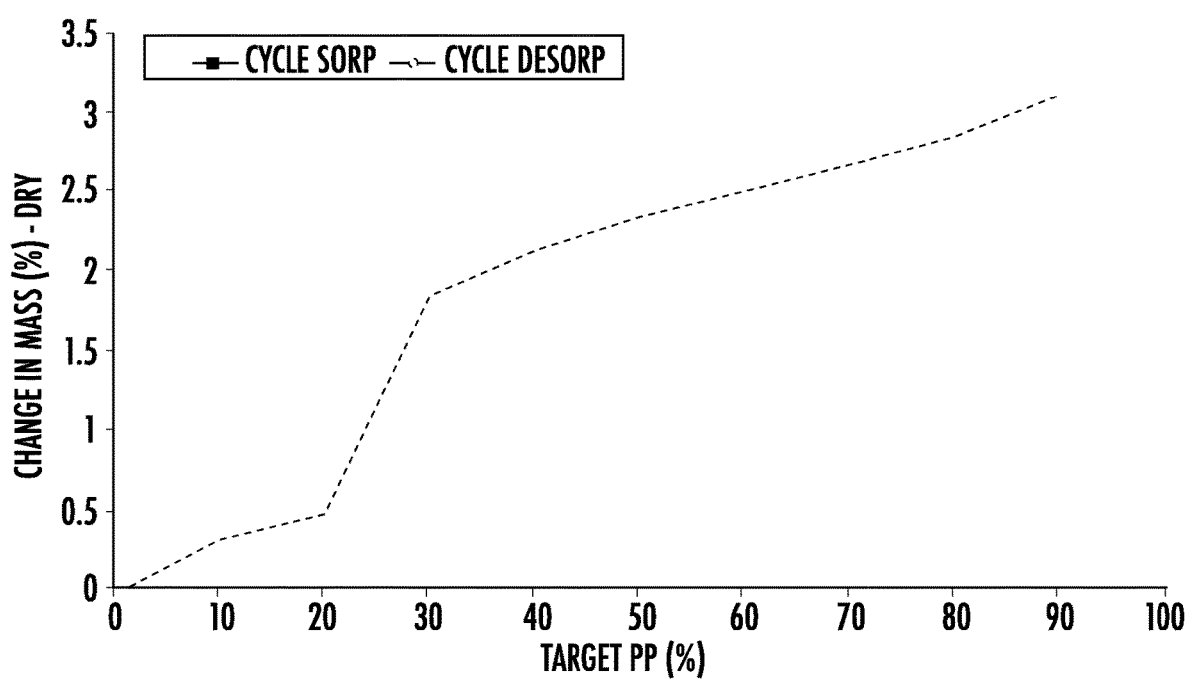
Figure 4C:
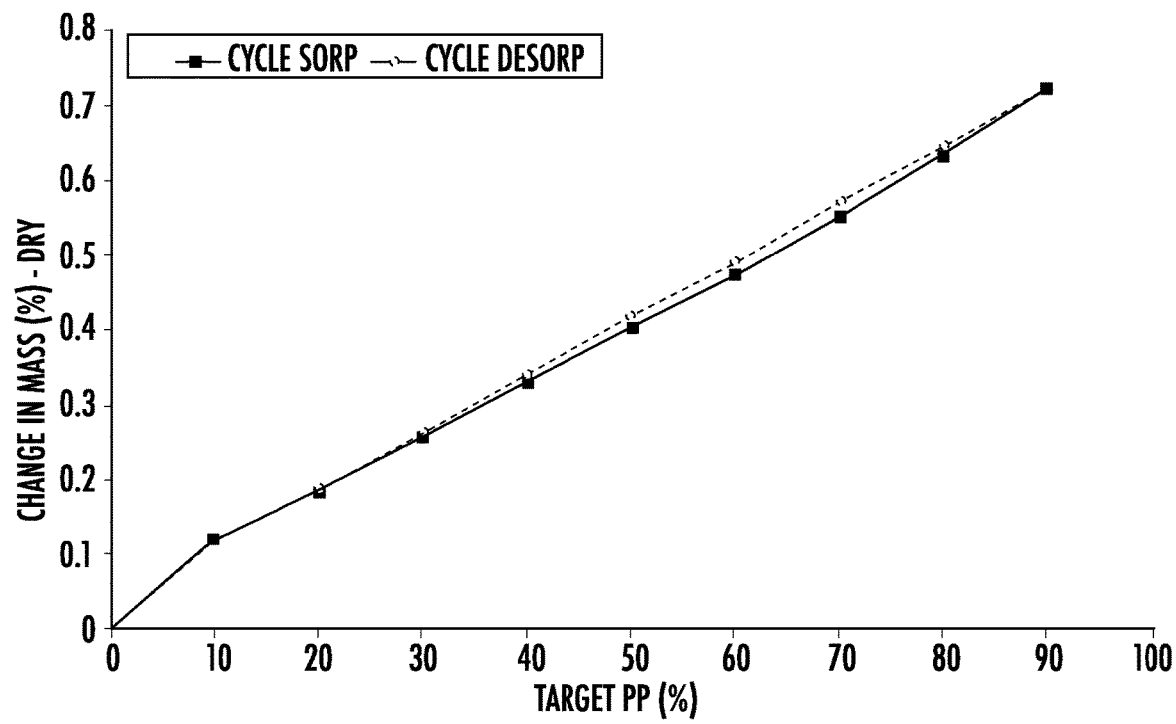
FIG. 4C shows DVS for the crystalline form prepared in Example 3.
Figure 4D:
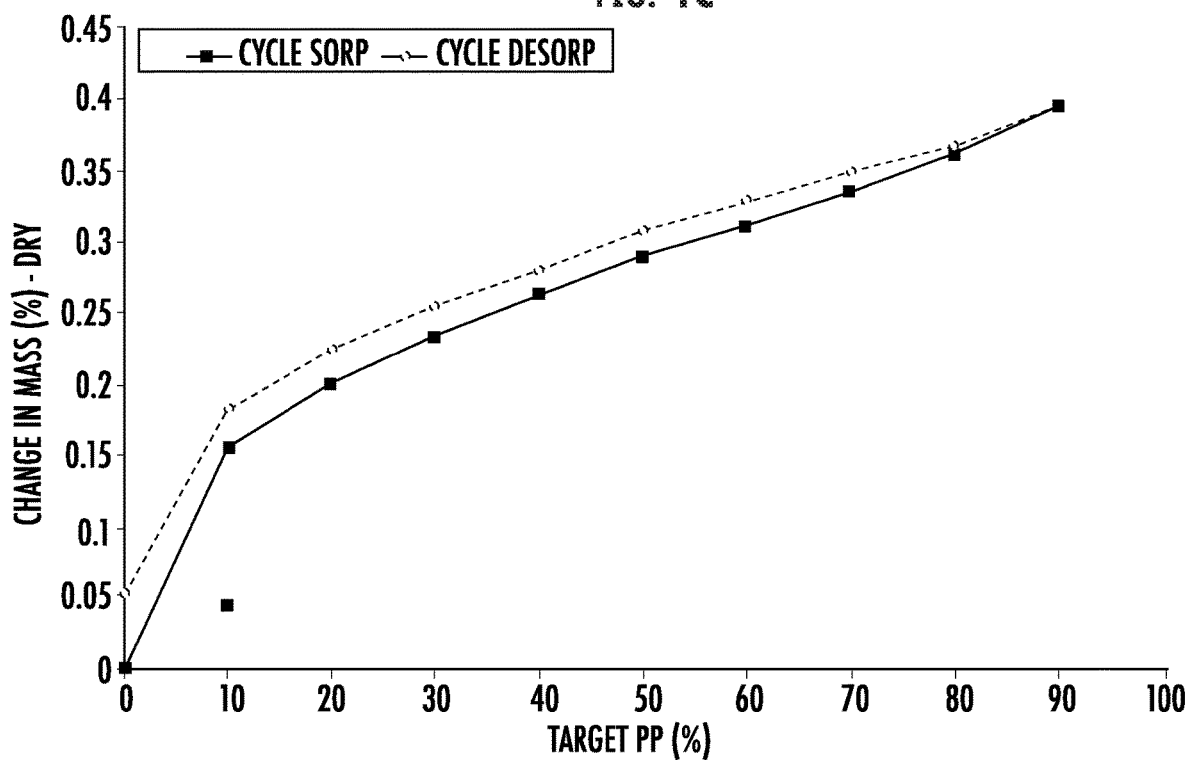
Figure 4E:
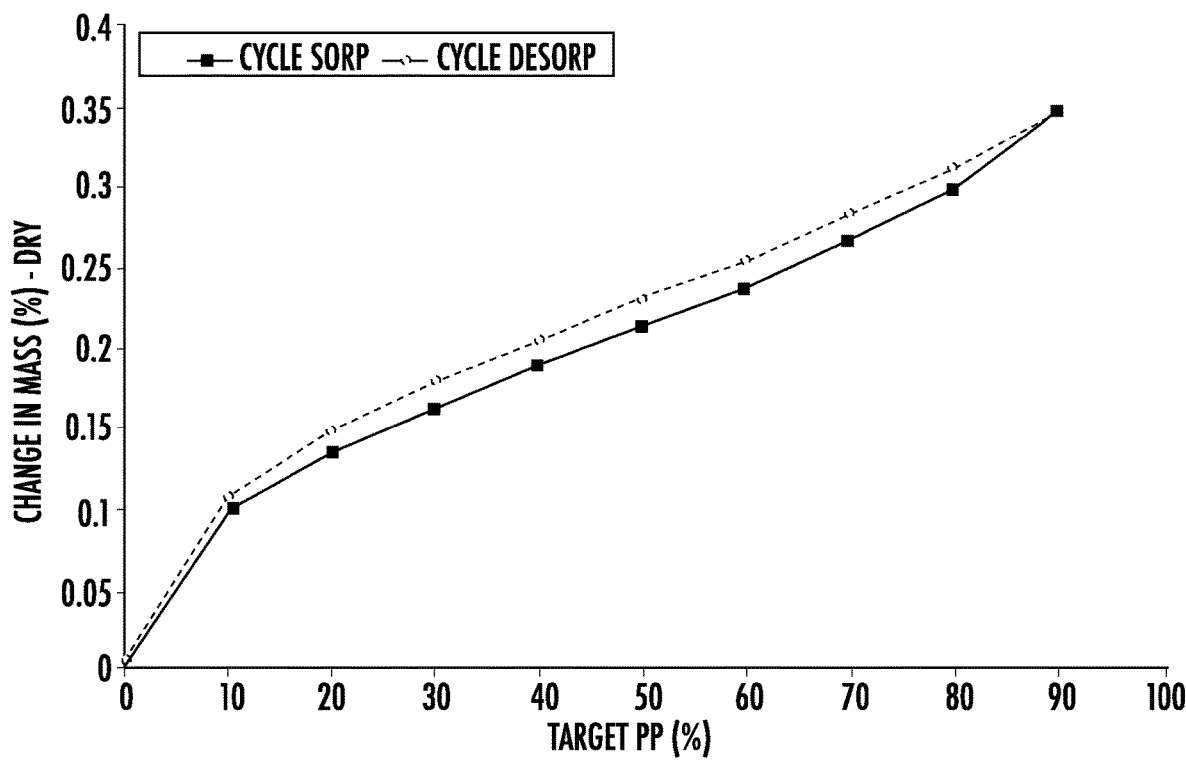
Figure 4F:
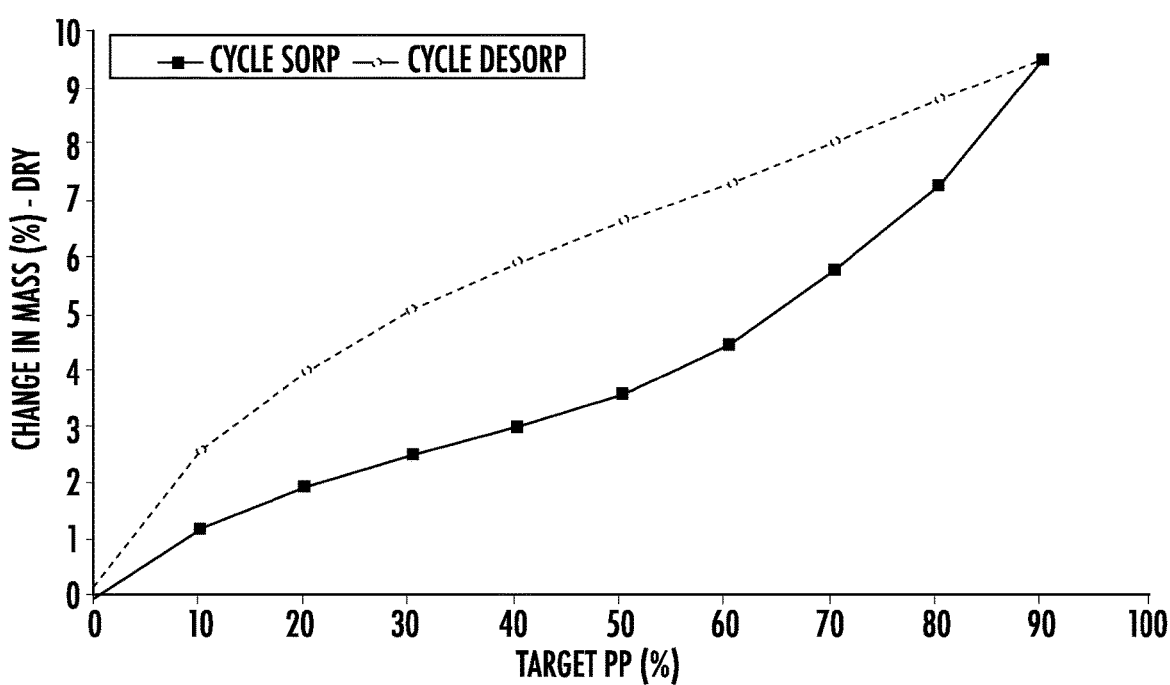
FIGS. 4F and 4G show the DVS graphs of the compound of chemical formula (1) and its amorphous hydrochloride salt form according to the comparative example.
Figure 4G:
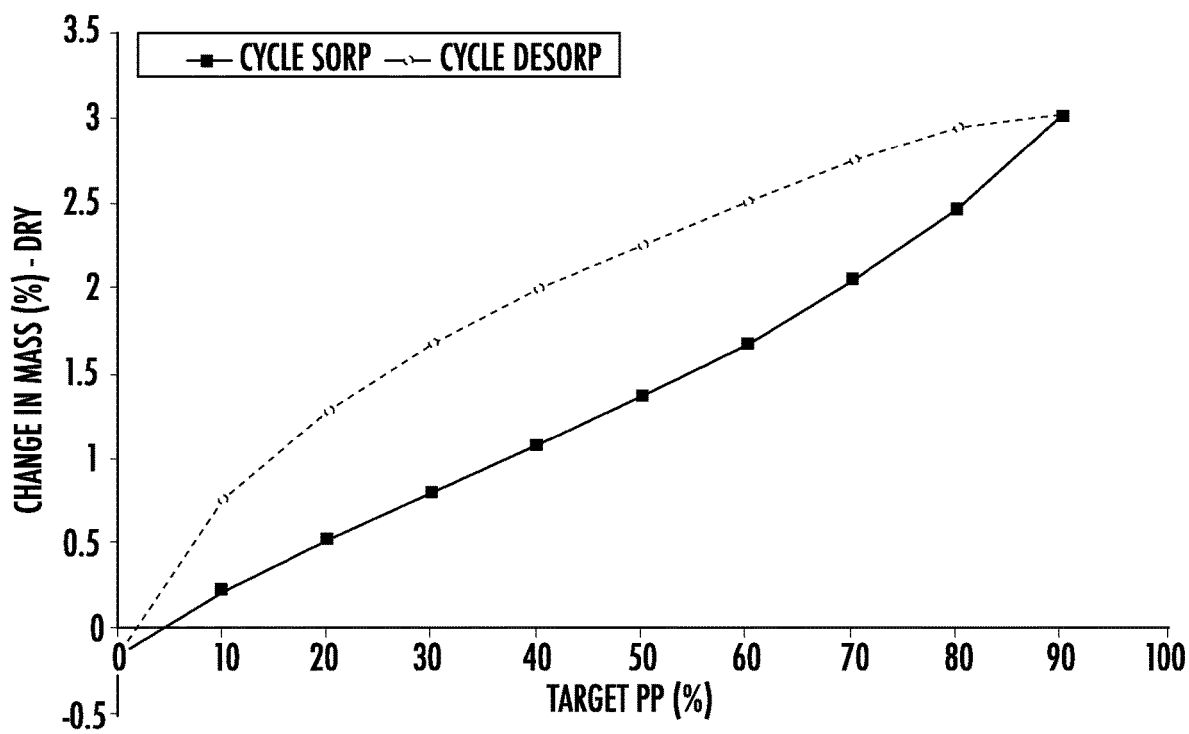

The analysis results of XRPD, ssNMR, DSC and DVS for the compound of chemical formula (1) prepared in Reference Example are shown in FIG. 1G, FIG. 2G and FIG. 4G, respectively.

The compound of chemical formula (1) prepared in Reference Example did not show any particular diffraction value in the XRPD spectrum, which shows a typical pattern of amorphous substances.

Also, the compound of Reference Example showed a broad peak in the spectrum of ssNMR, which is a typical peak pattern of amorphous structure.

Also, the compound of Reference Example did not exhibit any specific endotherm exotherm curve, as measured by the DSC (10° C./min).

Also, the compound of Reference Example exhibited a tendency to continuously absorb moisture of 1-3% at a relative humidity range of 10-90%, as measured by the DVS.

Also, the moisture content of the amorphous form was 2.1%, as measured by the Karl-Fischer moisture analyzer, and no characteristic melting point was observed.

Examples: Preparation of Crystalline Polymorphs of the Compound of Formula (I) and its Hydrochloride Salts Example 1. Preparation of the Crystalline Dihydrate ($2H_2O$) Form of the Compound of Chemical Formula (1)

To 10.0 g of the compound of chemical formula (1) of Reference Example, 80 mL of acetone and 20 ml of water were added, followed by completely dissolved the compound of chemical formula (1) by heating under reflux and then cooled to 20-25° C. and stirred for 4 hours. The resulting solid was filtered and washed with 20 mL of mixed solvent of 4:1 of acetone:water. The filtered solid was dried at 50° C. to give 10 g (yield: 93%) of the title compound.

Moisture content: 7.5% (theoretical value of the dihydrate: 6.83%)
Analysis of Characteristics The analysis results of XRPD, ssNMR, DSC and DVS for the crystalline form prepared in Example 1 are shown in FIGS. 1A, 2A, 3A and 4A, respectively.

Peaks with a relative intensity ($I/I_c$) of 15% or more of the crystalline form in the XRPD spectrum are summarized in Table 1 below. In the case of a peak of $I/I_o \geq 30\%$ or more, peaks at the diffraction angle ($2\theta\pm0.2°$) of 9.4, 11.4, 13.0, 16.1, 18.5, 19.3, 24.9 and 26.3° appeared.

TABLE 1

| 2 Θ (±0.2) | d | I/I$_o$(%) | 2 Θ (±0.2) | d | I/I$_o$(%) |
|---|---|---|---|---|---|
| 9.4 | 9.4 | 100 | 20.8 | 4.3 | 28.9 |
| 11.4 | 7.7 | 40.1 | 21.4 | 4.1 | 23.4 |
| 12.3 | 7.2 | 25.4 | 22.0 | 4.0 | 15.2 |
| 13.0 | 6.8 | 70.6 | 23.6 | 3.8 | 23.9 |
| 15.6 | 5.7 | 21.8 | 24.4 | 3.6 | 18.8 |
| 16.1 | 5.5 | 35.5 | 24.9 | 3.6 | 40.6 |
| 17.2 | 5.1 | 18.8 | 26.3 | 3.4 | 36.5 |
| 18.5 | 4.8 | 66.0 | 27.5 | 3.2 | 27.4 |
| 19.3 | 4.6 | 43.1 | 28.5 | 3.1 | 33.5 |

2 Θ: diffraction angle,
d: distance between crystal faces,
I/I$_o$ (%): relative intensity (I: intensity of each peak; I$_o$: intensity of the largest peak).

Peaks of the chemical shift (ppm±0.5 ppm) in the $^{13}$C CP/MAS TOSS ssNMR spectrum of the crystalline form are summarized in Table 2 below.

TABLE 2

| Peak # | Chemical Shift (ppm) | Peak # | Chemical Shift (ppm) | Peak # | Chemical Shift (ppm) |
|---|---|---|---|---|---|
| 1 | 29.4 | 8 | 95.5 | 15 | 131.0 |
| 2 | 32.1 | 9 | 101.0 | 16 | 144.9 |
| 3 | 33.2 | 10 | 105.7 | 17 | 147.7 |
| 4 | 40.5 | 11 | 109.2 | 18 | 150.7 |
| 5 | 45.5 | 12 | 124.4 | 19 | 151.9 |
| 6 | 55.6 | 13 | 126.6 | 20 | 156.2 |
| 7 | 73.8 | 14 | 128.7 | 21 | 165.4 | chemical shift (ppm ± 0.5 ppm).

The above crystalline form showed an endothermic peak of the lowest point at about 100.7° C. when running from a starting point of about 79° C. as measured by the DSC (10° C./min) and an endothermic peak of the lowest point at about 190.8° C. when running from a starting point of about 186.5° C. The endothermic peak at about 100.7° C., as measured by the DSC, means the dehydration point of the crystalline hydrate form of crystalline Form I of the compound of chemical formula (1), and the endothermic peak at about 190.8° C. means the melting point.

The crystalline form exhibited a moisture content (theoretical moisture content of 6.83%) of about 7.5% in the Karl-Fischer moisture analyzer and showed a condensation temperature of about 117-122° C. and a melting point of about 190-195° C.

The hygroscopic degree of the crystalline form was about 2% to 5% in the relative humidity range of 10%-90%, as measured by the DVS.

Example 2. Preparation of Crystalline Anhydrous Form I of the Compound of Chemical Formula (1)

To 5.0 g of the compound of chemical formula (1) obtained by the method of Example 1, 50 mL of acetone was added, and then stirred at 20-25° C. for 6 hours. The resulting solid was filtered and washed with 7.5 mL of acetone. The filtered solid was dried at 50° C. to obtain 3.7 g (yield: 80%) of the title compound.

Moisture content: 0.1%

Analysis of Characteristics

Analysis results of XRPD, ssNMR, DSC and DVS for the crystalline form prepared in Example 2 are shown in FIGS. 1B, 2B, 3B and 4B, respectively.

Peaks with a relative intensity (I/I$_o$) of 15% or more of the crystalline form in the XRPD spectrum are summarized in Table 3 below. In the case of a peak of I/I$_o$ 30% or more, peaks at the diffraction angle ($2\theta\pm0.2°$) of 6.0, 10.6, 10.9, 12.1, 16.0, 17.5, 18.3, 19.2, 20.3, 22.7, 23.7 and 26.3° appeared.

TABLE 3

| 2 Θ (±0.2) | d | I/I$_o$ (%) | 2 Θ (±0.2) | d | I/I$_o$ (%) |
|---|---|---|---|---|---|
| 6.0 | 14.6 | 75.6 | 20.3 | 4.4 | 58.1 |
| 10.6 | 8.3 | 47.1 | 20.8 | 4.3 | 18.6 |
| 10.9 | 8.1 | 48.8 | 22.1 | 4.0 | 26.7 |
| 12.1 | 7.3 | 62.2 | 22.7 | 3.9 | 100 |
| 13.0 | 6.8 | 25.0 | 23.7 | 3.8 | 55.2 |
| 16.0 | 5.5 | 57.6 | 24.2 | 3.7 | 15.1 |
| 17.5 | 5.1 | 32.0 | 26.3 | 3.4 | 62.2 |
| 18.3 | 4.9 | 85.5 | 28.1 | 3.2 | 18.0 |
| 18.7 | 4.7 | 23.3 | 32.1 | 2.8 | 17.4 |
| 19.2 | 4.6 | 36.0 | | | |

2 Θ: diffraction angle,
d: distance between crystal faces,
I/I$_o$ (%): relative intensity (I: intensity of each peak; I$_o$: intensity of the laraest peak).

Peaks of the chemical shift (ppm±0.5 ppm) in the $^{13}$C CP/MAS TOSS solid state nuclear magnetic resonance (ssNMR) spectrum of the crystalline form are summarized in Table 4 below.

TABLE 4

| Peak # | Chemical Shift (ppm) | Peak # | Chemical Shift (ppm) | Peak # | Chemical Shift (ppm) |
|---|---|---|---|---|---|
| 1 | 26.5 | 6 | 67.5 | 11 | 127.3 |
| 2 | 32.6 | 7 | 102.5 | 12 | 146.9 |
| 3 | 36.9 | 8 | 108.0 | 13 | 152.0 |
| 4 | 40.2 | 9 | 109.5 | 14 | 156.7 |
| 5 | 54.3 | 10 | 122.8 | 15 | 164.7 | chemical shift (ppm ± 0.5 ppm).

The above crystalline form exhibited an endothermic peak of the lowest point at about 190.8° C. when running from a starting point of about 185.8° C., as measured by the DSC (10° C./min), and the endothermic peak at about 190.8° C. means the melting point.

The crystalline form exhibited a moisture content of about 0.1%, as measured by the Karl-Fischer moisture analyzer, and showed a melting point at about 190-195° C.

The hygroscopic degree of the crystalline form was a level of about 0.3-0.5% in the relative humidity range of 10%-50%, as measured by the DVS, which is very low, and the hygroscopic degree in the range of 50-90% was measured to be a level of about 3%.

Example 3. Preparation of Crystalline Anhydrous Form II of the Compound of Chemical Formula (1)

To 2.0 g of the compound of chemical formula (1) of Example 2, 20 mL of acetonitrile was added, followed by heated and stirred at 70-80° C. for 2 hours and then stirred at 20-25° C. for 12 hours. The resulting solid was filtered and washed with 5 mL of acetonitrile. The filtered solid was dried at 50° C. to give 1.7 g (yield: 85%) of the title compound.

Moisture content: 0.3%.

Analysis of Characteristics

Analysis results of XRPD, ssNMR, DSC and DVS for the crystalline form prepared in Example 3 are shown in FIGS. 10C, 20, 30 and 40, respectively.

Peaks with a relative intensity (I/I$_o$) of 15% or more of the crystalline form in the XRPD spectrum are summarized in Table 5 below. In the case of a peak of I/I$_o$≥30% or more, peaks at the diffraction angle (2θ±0.2°) of 4.9, 5.9, 11.8, 18.8 and 19.9° appeared.

TABLE 5

| 2 ⊖ (±0.2) | d | I/I$_o$ (%) | 2 ⊖ (±0.2) | d | I/I$_o$ (%) |
|---|---|---|---|---|---|
| 4.9 | 18.2 | 50.3 | 19.5 | 4.6 | 25.7 |
| 5.9 | 15.1 | 35.6 | 19.9 | 4.5 | 32.6 |
| 11.8 | 7.5 | 100 | 22.0 | 4.0 | 17.3 |
| 13.9 | 6.4 | 24.5 | 25.2 | 3.5 | 26.1 |
| 14.7 | 6.0 | 24.3 | 25.5 | 3.5 | 23.3 |
| 16.1 | 5.5 | 24.3 | 27.0 | 3.3 | 18.5 |
| 18.8 | 4.7 | 38.6 | | | |

2 ⊖: diffraction angle,
d: distance between crystal faces,
I/I$_o$ (%): relative intensity (I: intensity of each peak; I$_o$: intensity of the largest peak).

Peaks of the chemical shift (ppm±0.5 ppm) in the $^{13}$C CP/MAS TOSS solid state nuclear magnetic resonance (ssNMR) spectrum of the crystalline form are summarized in Table 6 below.

TABLE 6

| Peak | Chemical Shift (ppm) | Peak # | Chemical Shift (ppm) | Peak # | Chemical Shift (ppm) |
|---|---|---|---|---|---|
| 1 | 25.1 | 13 | 98.9 | 25 | 129.2 |
| 2 | 26.9 | 14 | 101.0 | 26 | 144.0 |
| 3 | 30.5 | 15 | 102.8 | 27 | 144.9 |
| 4 | 32.5 | 16 | 104.5 | 28 | 145.7 |
| 5 | 35.3 | 17 | 105.2 | 29 | 147.1 |
| 6 | 36.8 | 18 | 106.2 | 30 | 151.1 |
| 7 | 41.0 | 19 | 107.0 | 31 | 153.1 |
| 8 | 54.3 | 20 | 110.2 | 32 | 155.1 |
| 9 | 55.1 | 21 | 122.0 | 33 | 156.7 |
| 10 | 57.5 | 22 | 124.6 | 34 | 163.2 |
| 11 | 68.3 | 23 | 126.4 | 35 | 165.2 |
| 12 | 70.0 | 24 | 127.5 | 36 | — | chemical shift (ppm ± 0.5 ppm).

The above crystalline form exhibited an endothermic peak of the lowest point at about 184.8° C. when running from a starting point of about 181.3° C., as measured by the DSC (10° C./min), and the endothermic peak at about 184.8° C. means the melting point.

The crystalline form exhibited a moisture content of about 0.3%, as measured by the Karl-Fischer moisture analyzer and showed a melting point of about 183-185° C.

The hygroscopic degree of the crystalline form was a level of about 0.7% in the relative humidity range of 10%-90%, as measured by the DVS, which is very low. The crystalline form was sufficiently stable at the long-term storage conditions (e.g., 25° C. and relative humidity of 60%), accelerated conditions (e.g., 40° C. and relative humidity of 75%), and harsh conditions (e.g., 60° C.).

Example 4. Preparation of Crystalline Monohydrochloride Monohydrate (1HCl·H$_2$O) Form of the Compound of Chemical Formula (1)

To 10 g of the compound prepared by the method of Reference Example or Examples 1 to 3, 100 ml of mixed solvent of ethanol:water (9:1) was added. 4.9 mL of 35% concentrated hydrochloric acid was added, and stirred at room temperature for 6 hours. The resulting solid was filtered and washed with 30 mL of ethanol. The filtered solid was dried at 50° C. to obtain 9.1 g (yield: 82%) of the title compound.

Moisture content: 3.2% (theoretical value of the monohydrate: 3.3%)

Ion chromatography: 6.5% (theoretical value of the monohydrochloride: 6.92%)

Analysis of Characteristics

Analysis results of XRPD, ssNMR, DSC and DVS for the crystalline form prepared in Example 4 are shown in FIGS. 1D, 2D, 3D and 4D, respectively.

Peaks with a relative intensity (I/I$_o$) of 15% or more of the crystalline form in the XRPD spectrum are summarized in Table 7 below. In the case of a peak of I/I$_o$≥30% or more, peaks at the diffraction angle (2θ±0.2°) of 8.9, 13.4, 14.1, 16.0, 19.8, 21.1, 21.7, 23.5, 25.7 and 32.7° appeared.

TABLE 7

| 2 ⊖ (±0.2) | d | I/I$_o$ (%) | 2 ⊖ (±0.2) | d | I/I$_o$ (%) |
|---|---|---|---|---|---|
| 8.9 | 10.0 | 61.5 | 21.7 | 4.1 | 42.0 |
| 10.5 | 8.4 | 18.3 | 22.0 | 4.0 | 18.3 |
| 12.3 | 7.4 | 28.4 | 22.4 | 4.0 | 15.4 |
| 12.6 | 7.0 | 17.8 | 23.5 | 3.8 | 100 |
| 13.4 | 6.6 | 94.7 | 24.2 | 3.7 | 21.3 |
| 14.1 | 6.3 | 35.5 | 25.7 | 3.5 | 52.1 |
| 16.0 | 5.5 | 36.1 | 27.5 | 3.2 | 20.7 |
| 16.4 | 5.4 | 17.8 | 28.0 | 3.2 | 17.2 |
| 17.3 | 5.1 | 21.3 | 28.7 | 3.1 | 20.1 |
| 18.1 | 4.9 | 27.2 | 29.9 | 3.0 | 25.4 |
| 19.3 | 4.6 | 18.3 | 30.6 | 2.9 | 21.9 |
| 19.8 | 4.5 | 32.0 | 32.3 | 2.7 | 20.1 |
| 21.1 | 4.2 | 92.3 | 32.7 | 2.7 | 30.2 |

2 ⊖: diffraction angle,
d: distance between crystal faces,
I/I$_o$ (%): relative intensity (I: intensity of each peak; I$_o$: intensity of the largest peak).

Peaks of the chemical shift (ppm±0.5 ppm) in the $^{13}$C CP/MAS TOSS solid state nuclear magnetic resonance (ssNMR) spectrum of the crystalline form are summarized in Table 8 below.

TABLE 8

| Peak # | Chemical Shift (ppm) | Peak # | Chemical Shift (ppm) | Peak # | Chemical Shift (ppm) |
|---|---|---|---|---|---|
| 1 | 27.0 | 10 | 96.3 | 19 | 126.0 |
| 2 | 33.5 | 11 | 98.2 | 20 | 133.2 |
| 3 | 39.0 | 12 | 99.6 | 21 | 134.7 |
| 4 | 40.3 | 13 | 104.1 | 22 | 145.8 |
| 5 | 41.6 | 14 | 104.9 | 23 | 148.7 |
| 6 | 42.0 | 15 | 105.9 | 24 | 149.2 |
| 7 | 56.4 | 16 | 123.3 | 25 | 152.9 |
| 8 | 72.2 | 17 | 124.3 | 26 | 157.8 |
| 9 | 73.0 | 18 | 124.6 | 27 | 164.5 | chemical shift (ppm ± 0.5 ppm).

The above crystalline form exhibited an endothermic peak of the lowest point at about 151.0° C. when running from a starting point of about 126.7° C., as measured by the DSC (10° C./min) and an endothermic peak at about 177.7° C. The endothermic peak at about 151.0° C. as measured by the DSC, means the dehydration point of the crystalline monohydrochloride monohydrate form, and the endothermic peak at about 177.7° C. indicates the melting point.

The crystalline form exhibited a moisture content of about 3.2% as measured by the Karl-Fischer moisture analyzer and showed a melting point of about 187-193° C.

The hygroscopic degree of the crystalline form was a level of about 0.4% in the relative humidity range of 10%-90%, as measured by the DVS, which is very low. It can be expected that the crystalline form absorbs moisture in long-term storage conditions (e.g., temperature of 25° C. and relative humidity of 60%) and accelerated conditions (e.g., temperature of 40° C. and relative humidity of 75%) to maintain the crystalline form of monohydrate.

Example 5. Preparation of Crystalline Anhydrous Monohydrochloride (1HCl) Form of the Compound of Chemical Formula (1)

To 20 g of the anhydrous compound 1 prepared by a method similar to that of Example 2, 60 mL of DMSO was added. 5.1 mL of 35% concentrated hydrochloric acid was added, and the mixture was stirred at room temperature for 6 hours. The resulting solid was filtered and washed with 40 mL of DMSO. The filtered solid was then dried at 50° C. to give 18.3 g (yield: 85%) of the title compound.

Moisture content: 0.1%

Ion chromatography: 6.6% (theoretical value of the monohydrochloride salt: 6.92%)

Additionally, to 20 g of the anhydrous compound 1 prepared by a method similar to that of Example 2, 60 mL of DMF was added. 5.1 mL of 35% concentrated hydrochloric acid was added, and stirred at room temperature for 6 hours. The resulting solid was filtered and washed with 40 mL of DMF. The filtered solid was dried at 50° C. to give 16.6 g (yield: 77%) of the title compound.

Analysis of Characteristics

Analysis results of XRPD, ssNMR, DSC and DVS for the crystalline form prepared in Example 5 are shown in FIGS. 1E, 2E, 3E and 4E, respectively.

Peaks with a relative intensity ($I/I_o$) of 15% or more of the crystalline form in the XRPD spectrum are summarized in Table 9 below. In the case of a peak of $I/I_o \geq 30\%$ or more, peaks at the diffraction angle ($2\theta \pm 0.2°$) of 9.5, 12.3, 13.0, 13.5, 14.2, 21.4, 23.0, 23.2, 23.5, 27.2 and 27.50° appeared.

TABLE 9

| 2 ⊖ (±0.2) | d | I/I$_o$ (%) | 2 ⊖ (±0.2) | d | I/I$_o$ (%) |
|---|---|---|---|---|---|
| 9.5 | 9.3 | 100 | 23.0 | 3.9 | 59.3 |
| 10.7 | 8.3 | 17.5 | 23.2 | 3.8 | 57.5 |
| 12.3 | 7.2 | 34.4 | 23.5 | 3.8 | 52.1 |
| 13.0 | 6.8 | 39.2 | 24.7 | 3.6 | 17.8 |
| 13.5 | 6.5 | 32.7 | 25.2 | 3.5 | 20.9 |
| 14.2 | 6.2 | 33.6 | 27.2 | 3.3 | 36.9 |
| 16.1 | 5.5 | 20.2 | 27.5 | 3.2 | 40.7 |
| 17.5 | 5.1 | 20.0 | 28.9 | 3.1 | 15.4 |
| 18.9 | 4.7 | 26.0 | 29.1 | 3.1 | 16.4 |
| 20.0 | 4.4 | 15.2 | 30.1 | 3.0 | 20.3 |
| 20.3 | 4.4 | 16.4 | 30.4 | 2.9 | 17.8 |
| 21.4 | 4.1 | 42.2 | 34.8 | 2.6 | 16.5 |
| 22.2 | 4.0 | 15.3 | | | |

2 ⊖: diffraction angle,
d: distance between crystal faces,
I/I$_o$ (%): relative intensity (I: intensity of each peak; I$_o$: intensity of the largest peak).

Peaks of the chemical shift (ppm±0.5 ppm) in the $^{13}$C CP/MAS TOSS solid state nuclear magnetic resonance (ssNMR) spectrum of the crystalline form are summarized in Table 10 below.

TABLE 10

| Peak # | Chemical Shift (ppm) | Peak # | Chemical Shift (ppm) | Peak # | Chemical Shift (ppm) |
|---|---|---|---|---|---|
| 1 | 27.9 | 8 | 99.8 | 15 | 134.8 |
| 2 | 31.7 | 9 | 106.4 | 16 | 146.9 |
| 3 | 37.0 | 10 | 109.0 | 17 | 151.3 |
| 4 | 41.2 | 11 | 122.5 | 18 | 156.9 |
| 5 | 56.2 | 12 | 125.3 | 19 | 158.7 |
| 6 | 71.4 | 13 | 129.0 | 20 | 163.0 |
| 7 | 96.1 | 14 | 130.6 | — | — | chemical shift (ppm ± 0.5 ppm).

The above crystalline form exhibited an endothermic peak of the lowest point at about 230.1° C. when running from a starting point of about 200.7° C., as measured by the DSC (10° C./min). The endothermic peak at about 230.1° C. means the melting point.

The crystalline form exhibited a moisture content of about 0.1% in the Karl-Fischer moisture analyzer and showed a melting point of about 238-243° C.

The hygroscopic degree of the crystalline form was at a level of about 0.35% in the relative humidity range of 10%-90%, as measured by the DVS, which is very low. The crystalline form did not absorb moisture in long-term storage conditions (e.g., temperature of 25° C. and relative humidity of 60%) and accelerated conditions (e.g., temperature of 40° C. and relative humidity of 75%) to maintain the crystalline form anhydrous.

Example 6. Preparation of the Amorphous Form of the Monohydrochlorde (1HCl) of the Compound of Chemical Formula (1)

5 g of the crystalline anhydrous form of the compound of formula 1 obtained in Example 5 was dissolved in 150 mL of methanol. The solution was filtered through the filter to remove foreign substances, and the filtrate was concentrated under reduced pressure to obtain 4.9 g (yield: 98%) of the title compound as a solid.

Moisture content: 1.2%

Analysis of Characteristics

Analysis results of XRPD, DVS and ssNMR for the amorphous form prepared in Example 6 are shown in FIGS. 1F, 2F, and 4F, respectively.

The amorphous form did not show any diffraction value in the XRPD spectrum.

In addition, the amorphous form exhibited a very high hygroscopic degree at the relative humidity range of 10-90%, as measured by the DVS. Through this, it is expected to be unstable by absorbing moisture under long-term storage conditions (25° C. temperature and relative humidity of 60%) and accelerated conditions (40° C. temperature and relative humidity of 75%). Actually, a moisture absorption of 7-9% b was confirmed under the 25° C., 60% relative humidity condition and the 40° C., 75% relative humidity condition.

In addition, the moisture content of the amorphous form was 1.2%, as measured by the Karl-Fischer moisture analyzer, and no characteristic melting point was observed.

Test Example 1: Comparative Test of Solubility of Amorphous Form and Crystalline Polymorphs of the Hydrochloride Salt To compare the solubility of amorphous hydrochloride salt form and crystalline hydrochloride salt polymorphs, each of the polymorphs and amorphous form of the hydrochloride salt of the compound of chemical formula (1) prepared in Examples 4 to 6 was used to prepare samples under the following conditions according to non-ionized water and acidity (pH). Thereafter, each solution was analyzed by high performance liquid chromatography (HPLC) according to the measurement conditions of the content of the compound of chemical formula (1) to measure the dissolved amount (LOD: 0.1 μg/mL) based on the compound of chemical formula (1). The results calculated from the measured values are shown in Table 11 below.

Specifically, 5 mg of each polymorph was added to 5 ml of water and mixed using a Voltamixer at 20-25° C. Thereafter, the filtrate obtained by filtrating using GH Polypro membrane Acrodisc, PALL (pore size 0.2 μm) was diluted with a dilution solvent for high performance liquid chromatography (HPLC) at a ratio of 1/100, to obtain the samples.

TABLE 11

| | Solubility (μg/mL) at 25° C. under a loading of 1.0 mg/mL | | | |
| --- | --- | --- | --- | --- |
| | Water | pH 1.2 | pH 2.0 | pH 4.0 |
| HCl amorphous | 53 | 274 | 213 | 34 |
| HCl cryst. hydrate | <LOD | 5 | 7 | 48 |
| HCl cryst. anhydrate | 20 | 92 | 140 | 74 |

As shown in the above Table 11, the solubility of the hydrochloride salt of the compound of chemical formula (1) was remarkably higher than that of the compound of chemical formula (1) (less than 1.0 μg/mL), and the crystalline anhydrous form of the hydrochloride salt among crystalline polymorphs showed the highest solubility in water.

Accordingly, the crystalline anhydrous hydrochloride salt form of the compound of chemical formula (1) is expected to be the most advantageous in terms of pharmaceutical composition when considering elution etc.

Test Example 2: Comparative Test of Stability of Amorphous Form and crystalline polymorphs of the hydrochloride salt To compare the stability of amorphous hydrochloride salt form and crystalline hydrochloride salt polymorphs, each of samples of the polymorphs and amorphous form of the hydrochloride salt of the compound of chemical formula (1) prepared in Examples 4 to 6 was left for 4 weeks under long term conditions (e.g., temperature of 25±2° C. and relative humidity of 60±5%) and accelerated conditions (e.g., temperature of 40° C. and relative humidity of 75%). Each sample was analyzed by high performance liquid chromatography (HPLC) according to the purity measurement conditions of the compound of chemical formula (1). The purity measurement values (%) are shown in Table 12 below.

TABLE 12

| | | Purity (HPLC, %) | | | | |
| --- | --- | --- | --- | --- | --- | --- |
| | Test conditions | Start | 3 days | Week 1 | Week 2 | Week 4 |
| HCl amorphous | 25 ± 2° C., 60 ± 5% RH | 98.0 | 98.0 | 98.0 | 97.9 | 97.9 |
| | 40 ± 2° C., 75 ± 5% RH | 98.0 | 97.9 | 97.9 | 97.8 | 97.6 |
| HCl cryst. hydrate | 25 ± 2° C., 60 ± 5% RH | 99.2 | 99.2 | 99.2 | 99.1 | 99.2 |
| | 40 ± 2° C., 75 ± 5% RH | 99.2 | 99.3 | 99.2 | 99.1 | 99.2 |
| HCl cryst. anhydrate | 25 ± 2° C., 60 ± 5% RH | 99.4 | 99.4 | 99.4 | 99.5 | 99.5 |
| | 40 ± 2° C., 75 ± 5% RH | 99.4 | 99.4 | 99.4 | 99.5 | 99.5 |

As shown in Table 12, the crystalline hydrochloride salt form of the compound of chemical formula (1) was stable compared to the amorphous hydrochloride salt form of the compound of chemical formula (1), and in particular, the crystalline anhydrous form of the hydrochloride salt of the compound of chemical formula (1) showed the best results.

Accordingly, through Comparative Tests 1 and 2, the crystalline anhydrous hydrochloride salt form of the compound of chemical formula (1) is expected to be the most advantageous in terms of the pharmaceutical composition when considering various physicochemical properties such as solubility, purity, stability, hygroscopicity, and melting point, etc.

What is claimed is:
1. Crystalline form of a compound of Chemical formula (1):

[Chemical formula (1)]

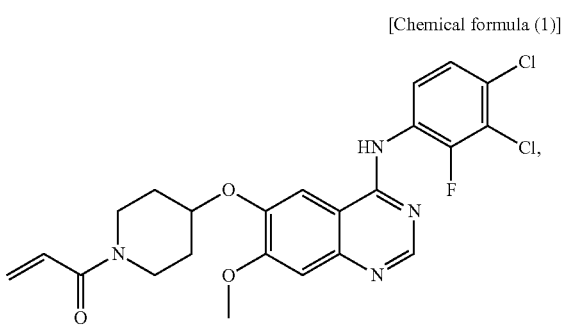 [SMILES: C=CC(=O)N1CCC(Oc2cc3c(Nc4ccc(Cl)c(Cl)c4F)ncnc3cc2OC)CC1]

wherein the chemical purity of the crystalline form is greater than about 80%, and
wherein the crystalline form is selected from the group consisting of
(a) a dihydrate (2H$_2$O) crystalline form of the compound of Chemical Formula (1) and the crystalline form, wherein the dihydrate crystalline form has an X-ray powder diffraction (XRPD) pattern comprising peaks at diffraction angle 2θ values of 9.4°±0.2°, 13.0°±0.2° and 18.5°±0.2° when irradiated with a Cu-Kα light source;
(b) an anhydrous Form I of the compound of Chemical Formula (1), wherein the anhydrous Form I has an XRPD pattern comprising peaks at diffraction angle 2 values θ of 6.0°±0.2°, 18.3°±0.2° and 22.7°±0.2° when irradiated with a Cu-Kα light source;
(c) an anhydrous Form II of the compound of Chemical Formula (1), wherein the anhydrous Form II has an XRPD pattern comprising peaks at diffraction angle 2θ values of 4.9°±0.2°, 5.9°±0.2° and 11.8°±0.2° when irradiated with a Cu-Kα light source;
(d) a monohydrochloride monohydrate (1HCl·1H$_2$O) crystalline form of the compound of Chemical Formula (1), wherein the monohydrochloride monohydrate crystalline form has an XRPD pattern comprising peaks at diffraction angle 2θ values of 8.9°±0.2°, 13.4°±0.2°, 21.1°±0.2° and 23.5°±0.2° when irradiated with a Cu-Kα light source; and
(e) an anhydrous monohydrochloride crystalline form of the compound of Chemical Formula (1), wherein the anhydrous monohydrochloride crystalline form has an XRPD pattern comprising peaks at diffraction angle 2 values θ of 9.5°±0.2°, 23.0°±0.2°, 23.2°±0.2° and 23.5°±0.2° when irradiated with a Cu-Kα light source.

2. The crystalline form of the compound of Chemical formula (1) of claim 1, wherein the chemical purity of the crystalline form is greater than 95%.

3. The crystalline form of claim 1, wherein the crystalline form is as described in (a).

4. The crystalline form of claim 1, therein the crystalline form is as described in (b).

5. The crystalline form of claim 1, wherein the crystalline form is as described in (c).

6. The crystalline form of claim 1, wherein the crystalline form is as described in (d).

7. The crystalline form of claim 1, wherein the crystalline form is as described in (e).

8. The crystalline form of claim 1, wherein the crystalline form is as described in (a), and wherein the crystalline form has a $^{13}$C solid state nuclear magnetic resonance (ssNMR) spectrum comprising peaks at the following chemical shifts: 147.7±0.5, 156.2±0.5 and 165.4±0.5 ppm.

9. The crystalline form of claim 1, wherein the crystalline form is as described in (b), and wherein the crystalline form has a $^{13}$C ssNMR spectrum comprising peaks at the following chemical shifts: 54.3±0.5, 127.3±0.5, 146.9±0.5 and 156.7±0.5 ppm.

10. The crystalline form of claim 1, wherein the crystalline form is as described in (c), and wherein the crystalline form has a $^{13}$C ssNMR spectrum comprising peaks at the following chemical shifts: 129.2±0.5, 153.1±0.5, 156.7±0.5 and 165.2±0.5 ppm.

11. The crystalline form of claim 1, wherein the crystalline form is as described in (d), and wherein the crystalline form has a $^{13}$C ssNMR spectrum comprising peaks at the following chemical shifts: 145.8±0.5, 157.8±0.5 and 164.5±0.5 ppm.

12. The crystalline form of claim 1, wherein the crystalline form is as described in (e), and wherein the crystalline form has a $^{13}$C ssNMR spectrum comprising peaks at the following chemical shifts: 146.9±0.5, 158.7±0.5 and 163.0±0.5 ppm.

13. A pharmaceutical composition comprising the crystalline form of claim 1, and at least one pharmaceutically acceptable carrier or diluent.

14. The pharmaceutical composition of claim 13, wherein the chemical purity of the crystalline form is greater than about 95%.

15. The pharmaceutical composition of claim 13, further comprising a non-metallic salt lubricant selected from the group consisting of glyceryl behenate, glyceryl palmitostearate, glyceryl monostearate, glyceryl trimyristate, glyceryl tristearate, sucrose fatty acid ester, palmitic acid, palmitoyl alcohol, stearic acid, stearyl alcohol, fumaric acid, polyethyleneglycol 4000, polyethyleneglycol 6000, polytetrafluoroethylene, starch, talc, hydrogenated castor oil, mineral oil, hydrogenated vegetable oil, silicon dioxide, and any combination thereof.

16. The pharmaceutical composition of claim 13, further comprising a metallic salt lubricant.

17. A method of treating a cancer in a subject comprising administering to the subject the pharmaceutical composition of claim 13, wherein the cancer is selected from the group consisting of non-small cell lung cancer, oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer and skin cancer.

18. The method of claim 17, wherein the cancer is non-small cell lung cancer.

19. A method of preparing the crystalline form of the compound of Chemical formula of claim 1, comprising
(1) preparing the dihydrate (2H$_2$O) of claim 3, comprising:
    (a) adding the compound of Formula 1 to a mixture of acetone and water, wherein the acetone and the water are in such a ratio that the compound cannot completely dissolve in the mixture at room temperature;
    (b) heating the mixture to a temperature wherein the compound completely dissolves; and
    (c) cooling down the mixture and removing the acetone and water to obtain the dihydrate (2H$_2$O) of the compound;
(2) preparing the anhydrous Form I of claim 4, comprising:
    (a) mixing the dihydrate (2H$_2$O) of the compound of claim 3 with acetone; and
    (b) isolating the anhydrous Form I of the compound;
(3) preparing the anhydrous Form II of claim 5, comprising:
    (a) mixing the anhydrous Form I of the compound of claim 4 with acetonitrile;
    (b) heating to above about 80° C.; and
    (c) cooling down and isolating the anhydrous Form II of the compound;
(4) preparing the monohydrochloride monohydrate (1HCl·1H$_2$O) of claim 6, comprising:
    (a) mixing the compound of Formula 1 with ethanol, water and aqueous hydrochloric acid; and
    (b) isolating the monohydrochloride monohydrate (1HCl·1H$_2$O) of the compound; or
(5) preparing the anhydrous monohydrochloride crystalline form of claim 7, comprising:
    (a) mixing an anhydrous compound of formula 1 with a non-protic polar solvent and a hydrochloric acid having a concentration of about 30% or more; and
    (b) isolating the anhydrous monohydrochloride of the compound.

20. The method of claim 19, comprising preparing the anhydrous monohydrochloride crystalline form of claim 7, wherein non-protic polar solvent is DMSO or DMF.

21. A kit comprising the crystalline form of claim 1, and at least one cytotoxic agent and/or at least one molecularly targeted agent, as the active ingredient, wherein the at least one cytotoxic agent is selected from the group consisting of taxanes, base analogs, VEGF inhibitors, platinum-based antineoplastic drugs and vinca alkaloids, and wherein the at least one molecularly targeted agent is selected from the group consisting of at least one epidermal growth factor receptor (EGFR) family inhibitor.

* * * * *